(12) United States Patent
Shah et al.

(10) Patent No.: US 11,654,214 B2
(45) Date of Patent: May 23, 2023

(54) CERAMIC-CONTAINING BIOACTIVE INKS AND PRINTING METHODS FOR TISSUE ENGINEERING APPLICATIONS

(71) Applicant: Northwestern University, Evanston, IL (US)

(72) Inventors: Ramille N. Shah, Oak Brook, IL (US); Adam E. Jakus, Chicago, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 365 days.

(21) Appl. No.: 15/963,348

(22) Filed: Apr. 26, 2018

(65) Prior Publication Data
US 2018/0243484 A1 Aug. 30, 2018

Related U.S. Application Data

(63) Continuation of application No. 14/450,220, filed on Aug. 2, 2014, now abandoned.

(60) Provisional application No. 61/993,360, filed on May 15, 2014, provisional application No. 61/861,545, filed on Aug. 2, 2013.

(51) Int. Cl.
| | |
|---|---|
| *A61L 27/56* | (2006.01) |
| *A61L 27/46* | (2006.01) |
| *A61L 27/54* | (2006.01) |
| *A61L 27/58* | (2006.01) |
| *C09D 167/04* | (2006.01) |
| *C09D 11/037* | (2014.01) |
| *C09D 11/104* | (2014.01) |
| *C09D 11/322* | (2014.01) |
| *B33Y 70/10* | (2020.01) |

(52) U.S. Cl.
CPC .............. *A61L 27/56* (2013.01); *A61L 27/46* (2013.01); *A61L 27/54* (2013.01); *A61L 27/58* (2013.01); *B33Y 70/10* (2020.01); *C09D 11/037* (2013.01); *C09D 11/104* (2013.01); *C09D 11/322* (2013.01); *C09D 167/04* (2013.01); *A61L 2300/442* (2013.01); *A61L 2430/02* (2013.01); *A61L 2430/06* (2013.01)

(58) Field of Classification Search
CPC ...... A61K 9/0024; A61K 6/802; A61K 31/74; A61K 9/209; A61K 51/1244; A61K 31/66; A61K 9/7007; A61K 8/0241; A61L 27/56; A61L 27/46; A61L 27/12; A61L 27/58; A61L 2430/02; A61L 2300/412; A61L 27/10; A61L 2430/34; A61L 2400/08; A61L 27/50

See application file for complete search history.

(56) References Cited

U.S. PATENT DOCUMENTS

| | | | |
|---|---|---|---|
| 5,518,680 A * | 5/1996 | Cima | A61F 2/022 264/401 |
| 7,087,109 B2 | 8/2006 | Bredt et al. | |
| 7,569,273 B2 | 8/2009 | Bredt et al. | |
| 9,327,448 B2 | 5/2016 | Shah et al. | |
| 2004/0241436 A1 * | 12/2004 | Hsieh | D01F 1/10 428/361 |
| 2005/0202058 A1 * | 9/2005 | Hiles | A61F 2/06 424/423 |
| 2006/0292350 A1 * | 12/2006 | Kawamura | A61L 27/12 428/189 |
| 2008/0145639 A1 | 6/2008 | Sun et al. | |
| 2009/0075382 A1 | 3/2009 | Sachlos | |
| 2009/0117087 A1 * | 5/2009 | Carroll | A61L 27/38 424/93.7 |
| 2010/0096596 A1 | 4/2010 | Lewis et al. | |
| 2010/0136114 A1 * | 6/2010 | Mao | A61K 35/44 424/486 |
| 2010/0279007 A1 | 11/2010 | Briselden et al. | |
| 2011/0064784 A1 * | 3/2011 | Mullens | B22F 3/1121 424/443 |
| 2011/0196094 A1 | 8/2011 | Hamad et al. | |
| 2013/0195955 A1 * | 8/2013 | Reichert | A61L 27/46 424/443 |
| 2013/0196405 A1 * | 8/2013 | Singh | B01D 69/02 435/182 |
| 2015/0037385 A1 | 2/2015 | Shah et al. | |
| 2015/0076732 A1 | 3/2015 | Kemmer et al. | |
| 2015/0125952 A1 | 5/2015 | Kim et al. | |
| 2015/0231302 A1 | 8/2015 | Duvall et al. | |

(Continued)

FOREIGN PATENT DOCUMENTS

| | | |
|---|---|---|
| CN | 103910901 A | 7/2014 |
| EP | 2195131 B1 | 10/2011 |

(Continued)

OTHER PUBLICATIONS

International Search Report & Written Opinion dated Mar. 15, 2019 for International patent application No. PCT/US2018/62595.

(Continued)

*Primary Examiner* — Tracy Liu

(74) *Attorney, Agent, or Firm* — Hahn Loeser & Parks LLP

(57) ABSTRACT

Ink formulations comprising bioactive particles, methods of printing the inks into three-dimensional (3D) structures, and methods of making the inks are provided. Also provided are objects, such as tissue growth scaffolds and artificial bone, made from the inks, methods of forming the objects using 3D printing techniques, and method for growing tissue on the tissue growth scaffolds. The inks comprise a plurality of bioactive ceramic particles, a biocompatible polymer binder, optionally at least one bioactive factor, and a solvent.

33 Claims, 33 Drawing Sheets

(56) References Cited

U.S. PATENT DOCUMENTS

2015/0315449 A1 11/2015 Kim
2016/0032062 A1 2/2016 Clauss et al.
2017/0081534 A1 3/2017 Shah et al.

FOREIGN PATENT DOCUMENTS

| JP | H09502999 A | 3/1997 |
| JP | 2006504813 A | 2/2006 |
| JP | 2010536694 A | 12/2010 |
| JP | 2010537679 A | 12/2010 |
| WO | WO 95/11007 A1 | 4/1995 |
| WO | WO 2004/028787 A1 | 4/2004 |
| WO | 2005114322 A2 | 12/2005 |
| WO | WO 2009/023226 A2 | 2/2009 |
| WO | 2009027525 A2 | 3/2009 |
| WO | WO 2004/027525 A2 | 3/2009 |

OTHER PUBLICATIONS

Levi et al., "Biodegradable Nano-Material Composites for Use in an Inkjet Printing System," Mater. Res. Soc. Symp. Proc., vol. 921, 2006, pp. 1-7.

Calvert et al., Solid freeform fabrication of organic-inorganic hybrid materials., Materials Science and Engineering: C 6.2, 1998, pp. 167-174.

Kyriakidou et al., Dynamic Co-Seeding of Osteoblast and Endothelial Cells on 3D Polycaprolactone Scaffolds for Enhanced Bone Tissue Engineering, Journal of Bioactive and Compatible Polymers, vol. 23, May 2008, pp. 227-243.

Ahn et al., Printed Origami Structures, Advanced Materials 22, May 25, 2010.

Hong et al., Microstructure and Mechanical Properties of Reticulated Titanium Scrolls, Advanced Engineering Materials, vol. 13, No. 12, 2011, pp. 1122-1127.

Yeo et al., Preparation and Characterization of 3D Composite Scaffolds Based on Rapid-Prototyped PCL-TCP Struts and Electrospun PCL Coated with Collagen and HA for Bone Regeneration, Chem. Mater., vol. 24, Jul. 5, 2011, pp. 903-913.

Jakus et al., 3D-Bioplotted Elastic Bone Scaffolds for Tissue Engineering Applications, Poster Presentation, Oral Biology Centennial, University of Chicago, Jun. 19, 2013.

Jakus et al., A Single Platform 3D-Printing Approach for Fabricating Tissue Engineering Bio-Scaffolds from Multiple Material Systems, Oral Presentation, Materials Science and Engineering 2013 Hilliard Symposium, Northwestern University, Evanston, May 16, 2013.

Jakus et al., Biochemically Active Bioplotted Elastic Hydroxyapatite-Based Tissue Engineering Scaffolds: Structural, Mechanical, and in vitro Evaluation, Abstract for Presentation at TMS Pacific Rim International Congress on Advanced Materials and Processing Waikoloa, HA, Aug. 7, 2013.

Jakus et al., Bioplotted Ceramics and Metals: A Universal Technique for Fabricating Complex, Ordered, and Functional Scaffolds, The 8th Pacific Rim International Congress on Advanced Materials and Processing, Abstract, Aug. 1, 2013.

Jakus et al., Bioplotted Elastic Hydroxyapatite-Based Tissue Engineering Scaffolds, Oral Presentation, TMS Pacific Rim International Congress on Advanced Materials and Processing, Waikoloa, HA, Aug. 6, 2013.

Shuai et al., Fabrication of poros polyvinyl alcohol scaffold for bone tissue engineering via selective laser sintering, Biofabrication, vol. 5, No. 015014, Feb. 6, 2013, pp. 1-8.

Ahn et al., Carbon-nanotube-interfaced glass fiber scaffold for regernation of transected sciatic nerve, Acta Biomaterialia 13, Nov. 21, 2014, pp. 324-334.

Guo et al., Properties of polylactide inks for solvent-cast printing of three-dimensional freeform microstructures, Langmuir, Jan. 11, 2014, vol. 30, No. 4, pp. 1142-1150.

Jakus et al., 3D Printed Solid Oxide Fuel Cells from High Particle Content Liquid Inks, MRS Fall 2014 Meeting, Dec. 3, 2014.

Jakus et al., 3D-Printed Hyperelastic Bone for Hard-Tissue Engineering Applications, Abstract for Presentation at Hilliard Symposium, Northwestern University, May 15, 2014.

Jaycox et al., 3-D Printing Lunar and Martian Dusts From Liquid 3D-Inks, Poster Presentation at ASM Chicago on Apr. 8, 2014.

Jakus et al., Three-dimensional printing of high-content graphene scaffolds for electronic and biomedical applications, ACS Nano, Apr. 10, 2015, vol. 9, No. 4, pp. 4636-4648.

Michna et al., Concentrated hydroxyapatie inks for direct-write assembly of 3-D periodic scaffolds, Biomaterials, vol. 26, Apr. 21, 2015, pp. 5632-5639.

* cited by examiner

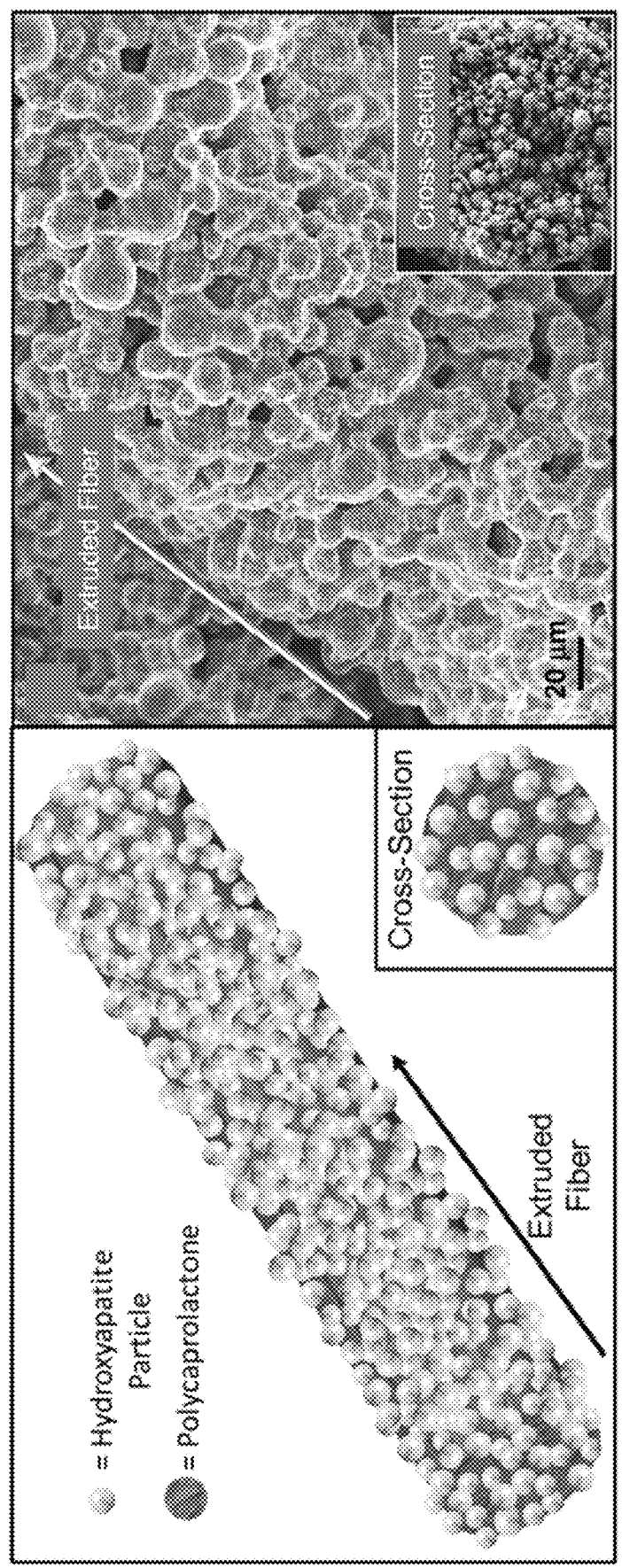

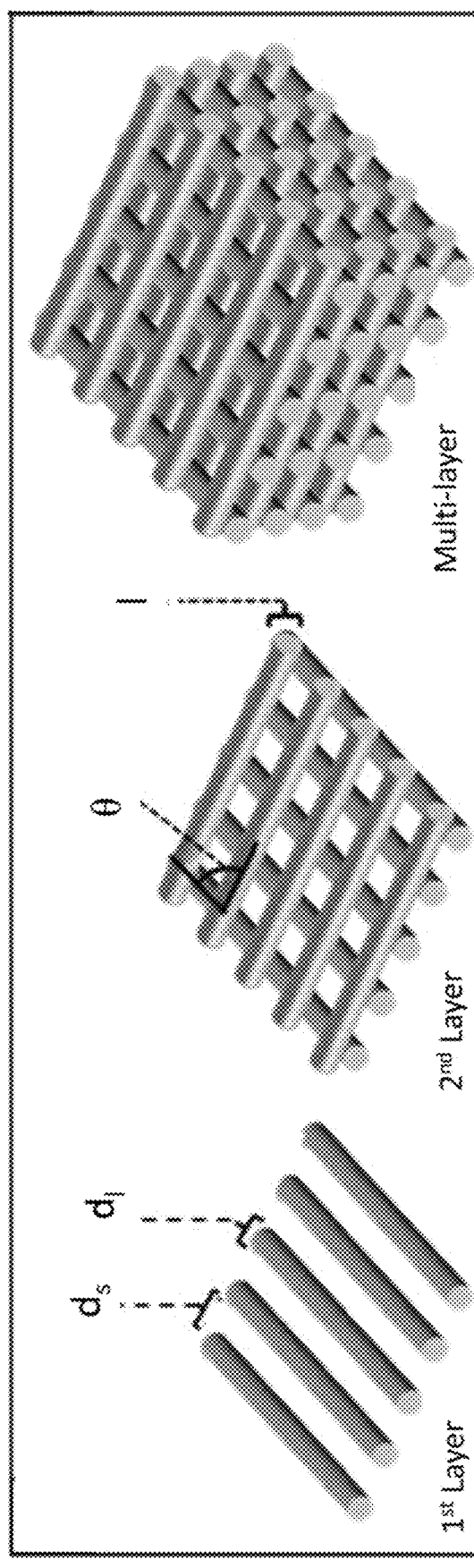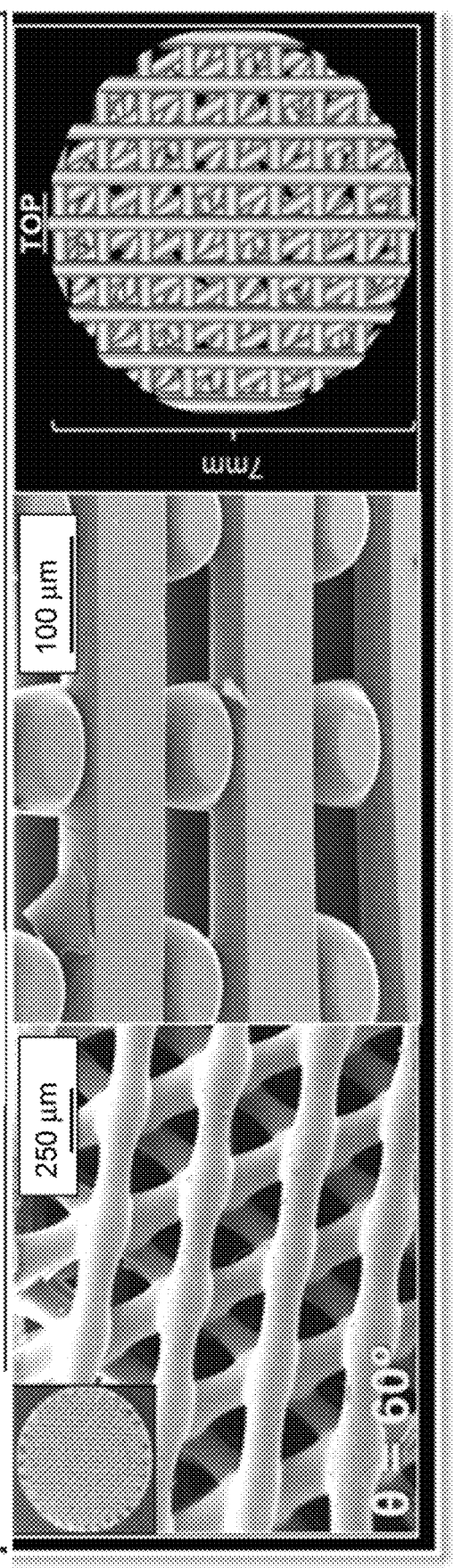
FIG. 2A FIG. 2B FIG. 2C FIG. 2D

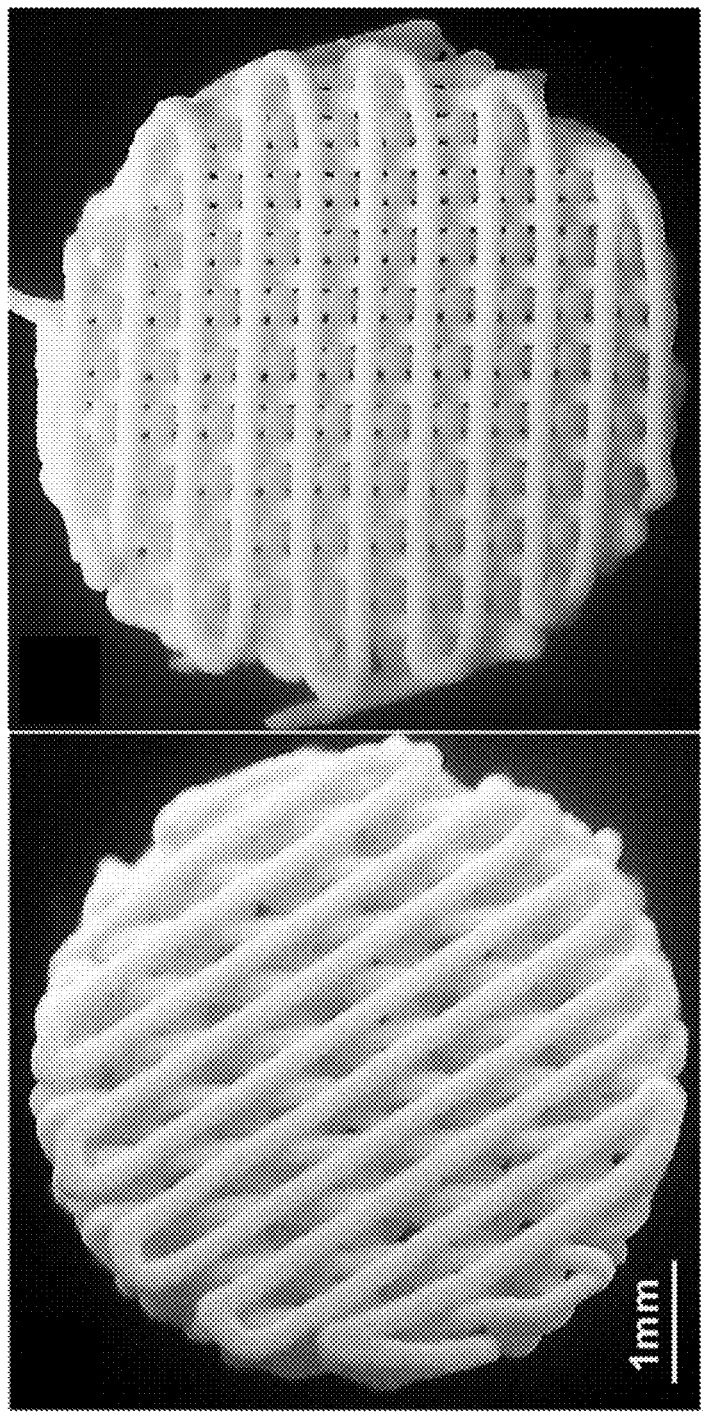

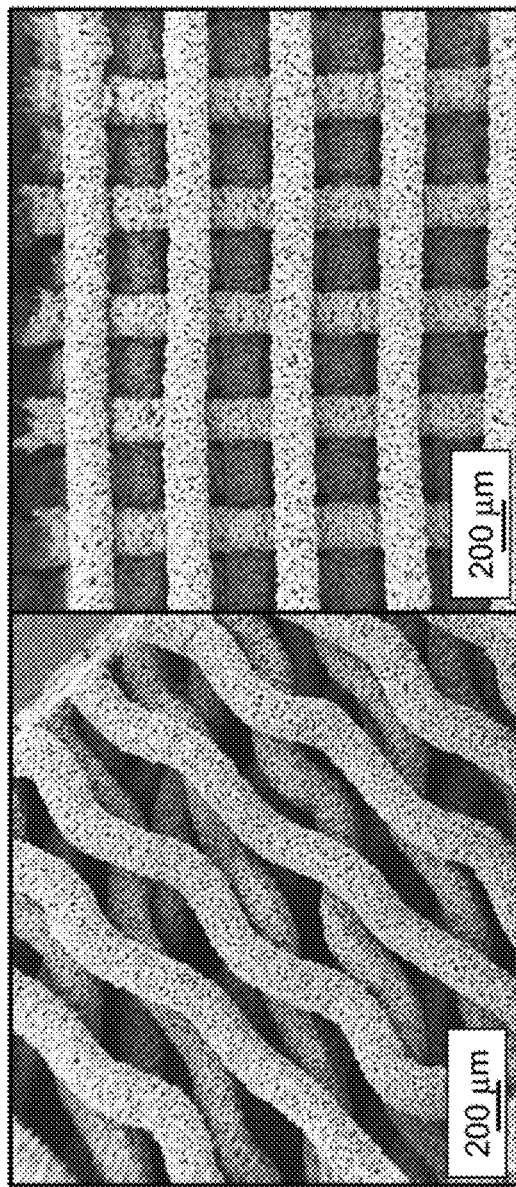
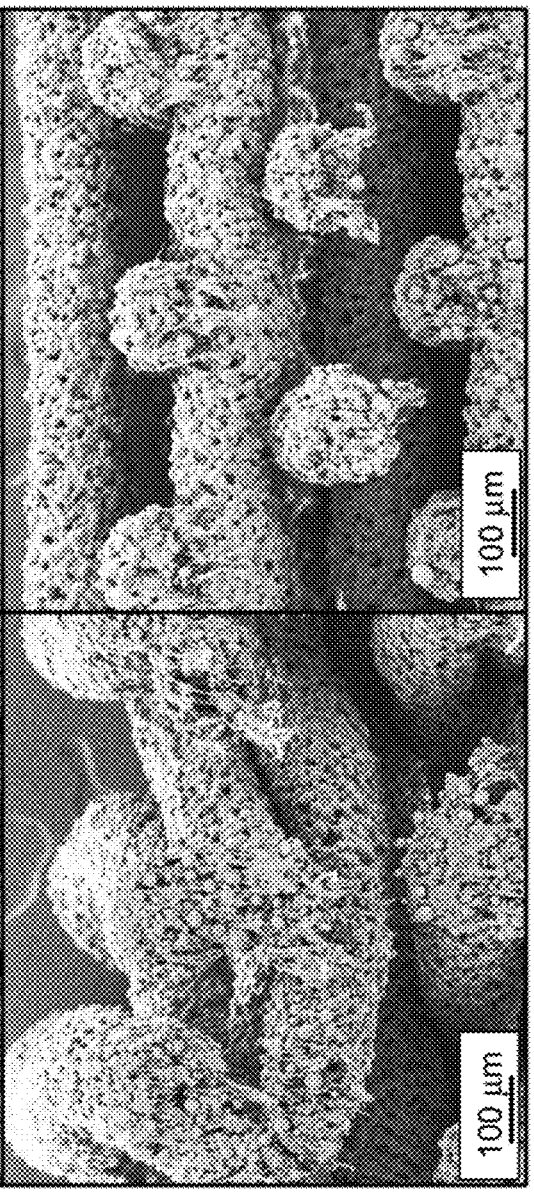

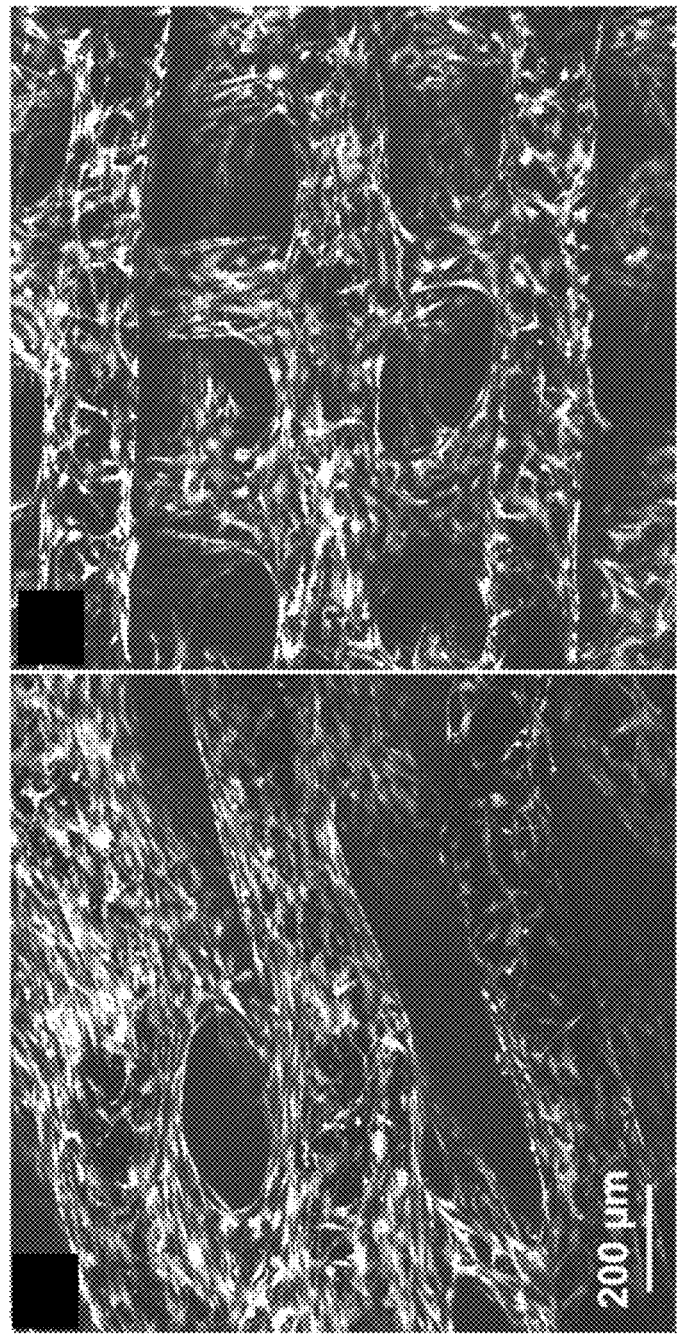

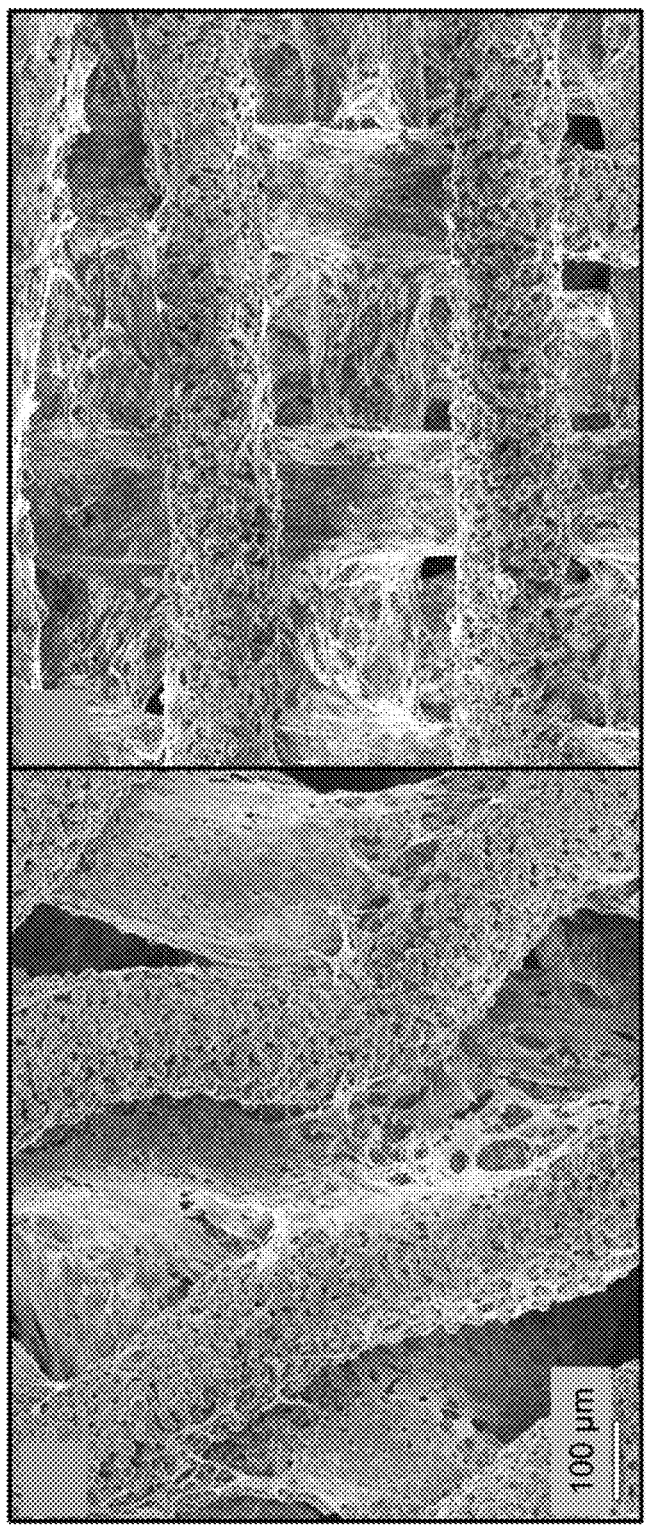

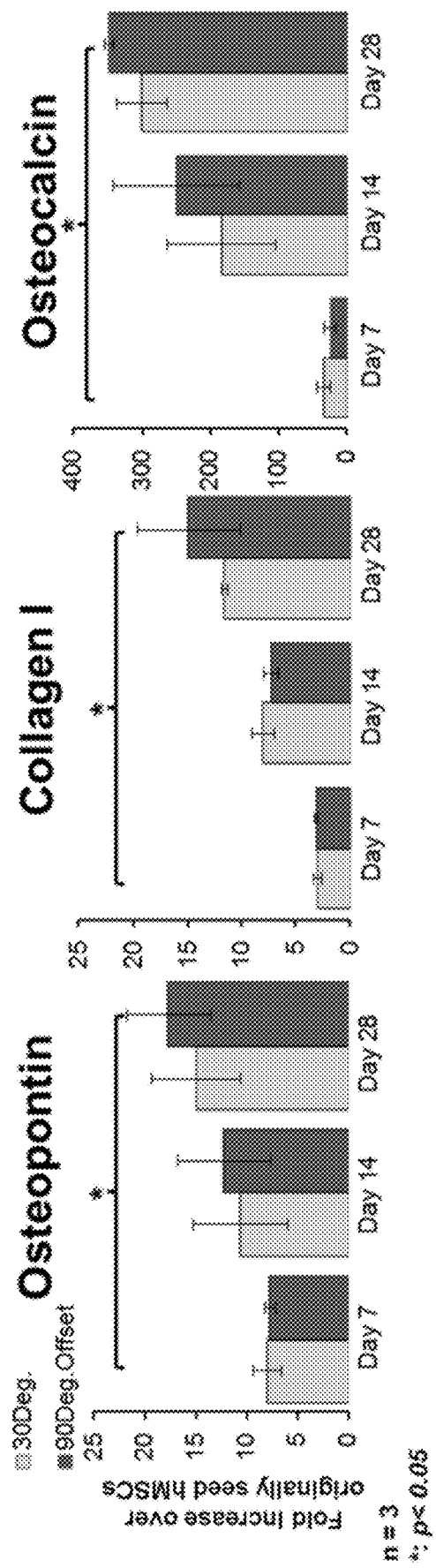

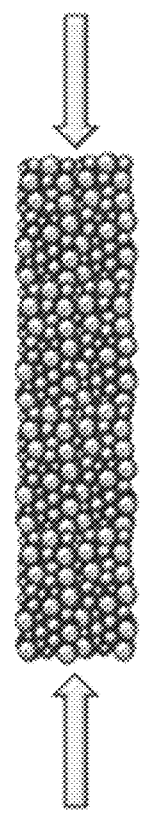
FIG. 18A
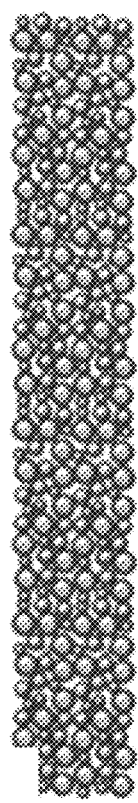
FIG. 18B
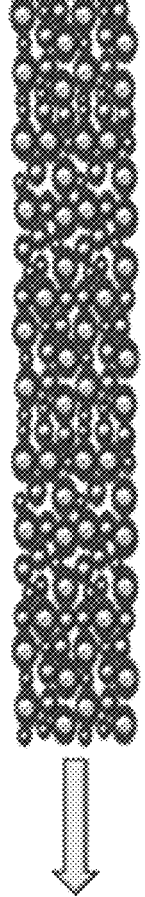
FIG. 18C
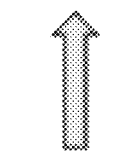
FIG. 18D
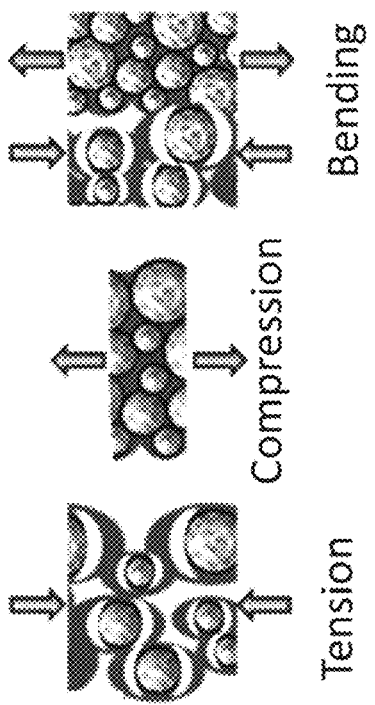
FIG. 19
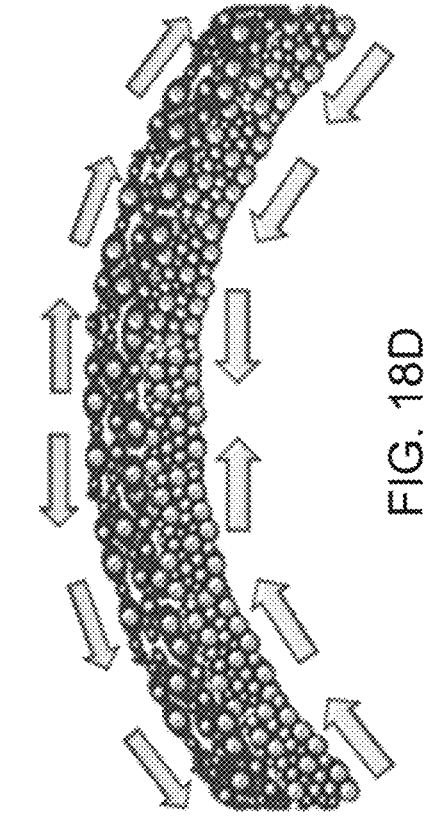

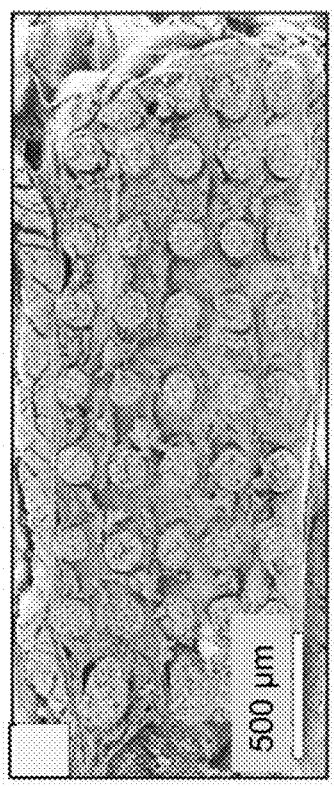
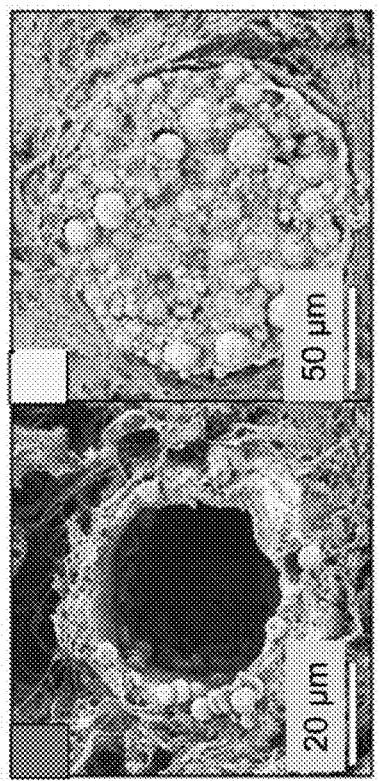
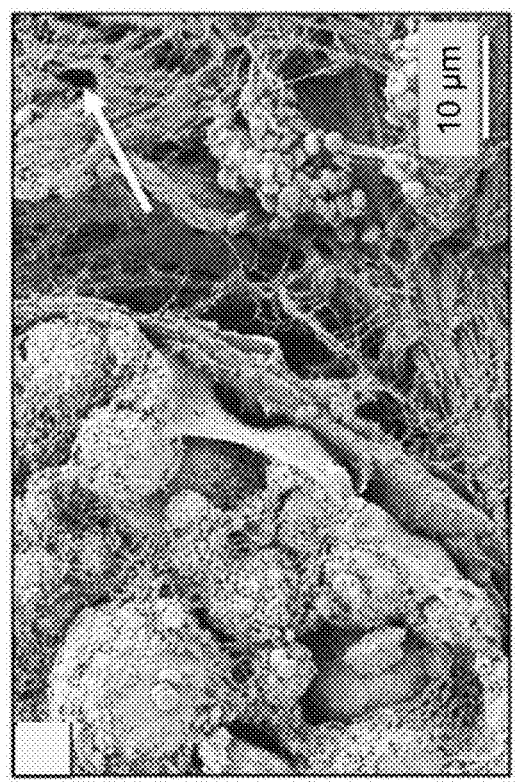
FIG. 23A
FIG. 23B
FIG. 23C
FIG. 23D

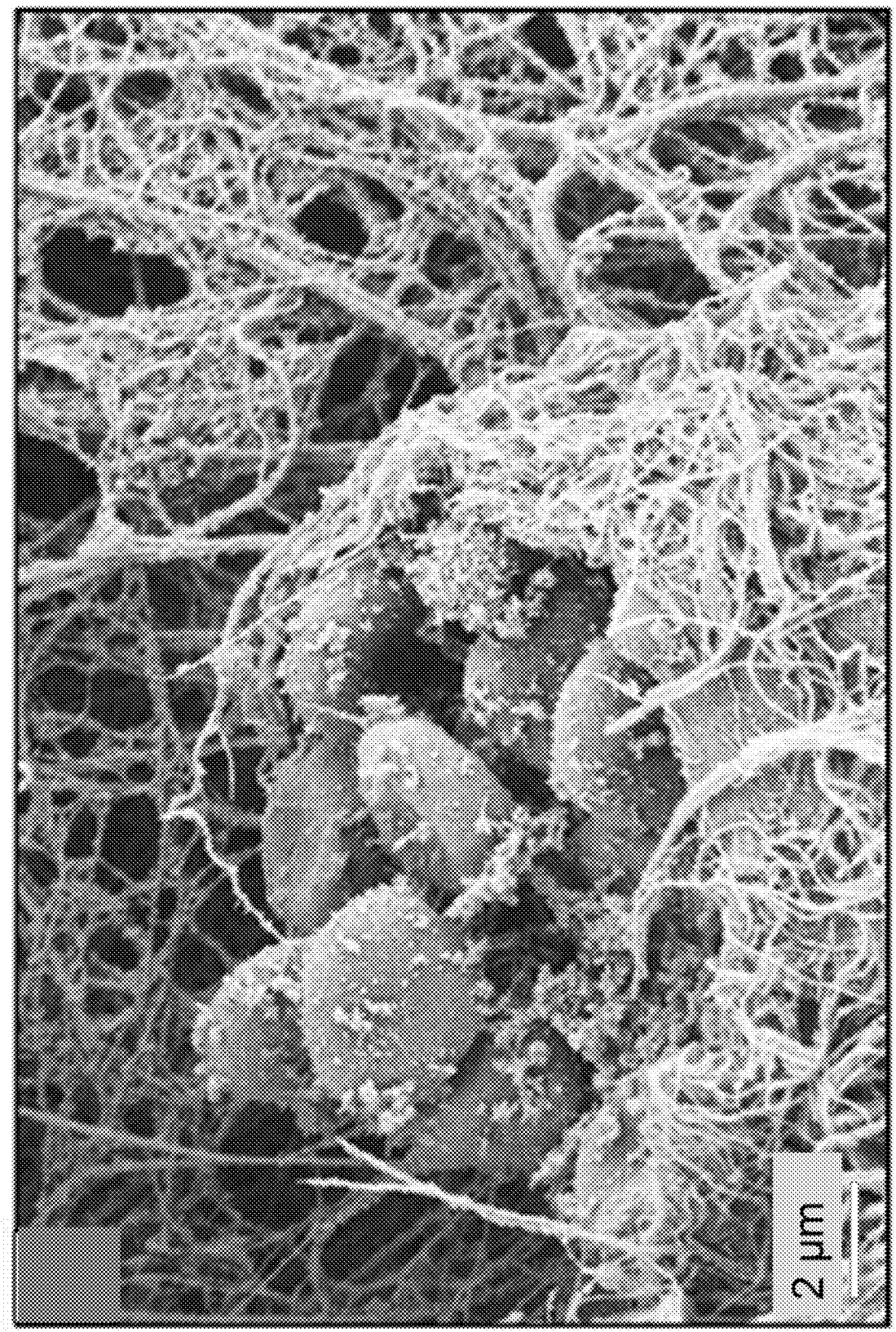

CERAMIC-CONTAINING BIOACTIVE INKS AND PRINTING METHODS FOR TISSUE ENGINEERING APPLICATIONS

CROSS-REFERENCE TO RELATED APPLICATIONS

The present application is a continuation of U.S. patent application Ser. No. 14/450,220 that was filed Aug. 2, 2014, the entire contents of which are incorporated herein by reference; which claims priority to U.S. provisional patent application No. 61/861,545 that was filed Aug. 2, 2013 and U.S. provisional patent application No. 61/993,360 that was filed on May 15, 2014; the entire contents of each of these applications is incorporated herein by reference.

BACKGROUND

Composite scaffolds of hydroxyapatite (HAp) and polycaprolactone (PCL) or polylactic-co-glycolic acid (PLGA) have been developed. However, these composites have been formed utilizing hot-melt three-dimensional printing to produce scaffolds composed primarily of PCL or PLGA with embedded HAp. This technique has many drawbacks: 1) hot-melt printing prohibits incorporation of bioactive factors directly into the material; 2) the extrusion process relies on the hot melt suspension to be extrudable, which cannot be practically accomplished when the weight fraction of solid HAp particles is greater than approximately 0.5; 3) because the material is primarily PCL, HAp particles are encapsulated and are not exposed on the surface of the material, meaning that the surface properties of the material are those of PCL (i.e., smooth and not amenable to cell adhesion); 4) final objects made from the composites are stiff and brittle, preventing reshaping or modification after fabrication; and 5) a hot melt suspension cannot be co-printed into objects along with temperature sensitive materials, such as hydrogels or cell-encapsulated materials.

SUMMARY

Ink formulations comprising bioactive particles, methods of forming the inks into structures, and methods of making the inks are provided. Also provided are porous tissue growth scaffolds made from the inks, methods of forming the tissue growth scaffolds using 3D printing techniques, and methods for growing tissue on the tissue growth scaffolds.

One embodiment of an ink comprises bioactive ceramic particles, such as hydroxyapatite particles; a biocompatible polymer binder, such as polycaprolactone or polylactic-co-glycolic acid; optionally at least one bioactive factor; and a solvent. In some embodiments, the ink comprises a mixture of the solvents (for example, two or three solvents), as in the case when a graded solvent is used. The inks may have a high concentration of bioactive ceramic particles. For example, some embodiments of the inks comprise at least 70 weight percent of the bioactive ceramic, based on the total combined weight of the bioactive ceramic particles and the biocompatible polymer binder. This includes embodiment of the inks that comprise at least 90 weight percent of the bioactive ceramic, based on the total combined weight of the bioactive ceramic particles and the biocompatible polymer binder.

One embodiment of a method of forming an ink comprises dissolving a biocompatible polymer binder in a first solvent and, optionally, mixing one or more bioactive factors into the solvent to form a solution; dispersing bioactive ceramic particles into a second solvent to form a dispersion; and mixing the solution and the dispersion to form the ink.

One embodiment of a method of printing a three-dimensional object using the inks comprises printing one or more layers of the ink on a substrate and allowing the printed layers to dry.

One embodiment of a porous scaffold comprises a plurality of layers configured in a vertical stack, each layer comprising a material comprising a plurality of bioactive ceramic particles in a biocompatible polymer binder and, optionally, one or more bioactive factors.

One method of growing tissue on the scaffold comprises seeding the scaffold with tissue-forming cells, or cells that are precursors to tissue forming cells, and culturing the seeded-scaffold in a cell growth culture medium.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 1(A). Schematic representation with cross-section of hydroxyapatite-polycaprolactone (HAPCL) composite fiber. FIG. 1(B) scanning electron microscopy images of HAPCL composite fiber with cross-section (inset).

FIG. 2(A). Schematic illustration of the extrusion-based printing processes: single fibers, with thickness $d_f$, are deposited $d_s$ distance apart. Subsequent layers are deposited 1 distance ($l \sim d_f$) at orientation, $\theta$, with respect to first layer. This process continues until the final structure is complete.

FIG. 2(B). Top view of a scaffold printed via layer-by-layer extrusion.

FIG. 2(C). Side view of a scaffold printed via layer-by-layer extrusion.

FIG. 2(D). Schematic drawing of the top view of a scaffold printed via layer-by-layer extrusion.

FIG. 3(A). Image of 3D-Printed HAPCL scaffold with differing pore architecture for 8-layer 30° advancing angle layers. FIG. 3(B). Image of 3D-Printed HAPCL scaffold with differing pore architecture for 8-layer 90° advancing angle with 250 µm offset every other layer.

FIGS. 4A-D. Scanning electron micrographs of 3D-printed HAPCL scaffolds with differing pore architecture. In FIG. 4(A), the printed fibers are non-linear along their longitudinal axes. FIG. 4(C) is a cross-sectional view of the scaffold of FIG. 4(A). In FIG. 4(B) the fibers in each layer are oriented substantially parallel, while the fibers in adjacent layers are oriented substantially perpendicular. FIG. 4(D) is a cross-sectional view of the scaffold of FIG. 4(B).

FIG. 6(A). Laser scanning fluorescent confocal microscopy live/dead reconstructions of hMSCs 7 days after seeding on 30° HAPCL. FIG. 6(B). Laser scanning fluorescent confocal microscopy live/dead reconstructions of hMSCs 7 days after seeding on 90° offset HAPCL. Bright Areas=Live Cells.

FIG. 7(A). Scanning electron micrograph of hMSCs 7 days after seeding on 30° HAPCL. FIG. 7(B). Scanning electron micrograph of hMSCs 7 days after seeding on 90° offset HAPCL.

FIG. 9(A). hMSC expression of osteopontin on 3D-Bioplotted 30° HAPCL and 90° offset HAPCL at 7, 14, and 28 days after seeding in simple proliferation media, not a osteogenic differentiation media. FIG. 9(B). hMSC expression of collagen on 3D-Bioplotted 30° HAPCL and 90° offset HAPCL at 7, 14, and 28 days after seeding in simple proliferation media, not a osteogenic differentiation media. FIG. 9(C) hMSC expression of osteocalcin on 3D-Bioplotted 30° HAPCL and 90° offset HAPCL at 7, 14, and 28 days after seeding in simple proliferation media, not a osteogenic differentiation media.

FIG. 18(A). Schematic representation of ceramic particle and elastomer distribution in unloaded fiber. FIG. 18(B). Schematic representation of ceramic particle and elastomer distribution in compressed fiber. FIG. 18(C). Schematic representation of ceramic particle and elastomer distribution in stretched fiber. FIG. 18(D). Schematic representation of ceramic particle and elastomer distribution in bent fiber. Arrows represent tensile and compressive loads.

FIG. 19. Upon unloading, a restoring force opposite in direction to the original tensile, compressive, or bending loads causes the fiber to return to its initial morphology.

FIG. 23(A). SEM image of an entire HAPLGA scaffold cross-section, with incision site towards top of image, illustrating tissue infiltration. FIG. 23(B). SEM image of a cross-section of representative blood vessels found throughout the HAPLGA scaffold. FIG. 23(C). Magnified view of single HAPLGA strut cross-sections and surrounding tissues. FIG. 23(D). High-magnification image of HAPLGA strut-tissue interfaces and formed capillaries (arrow).

FIG. 25(B). SEM micrograph of a cut blood vessel which was in the middle of transporting red blood cells as well as other cells (monocyte, arrows) from explanted HAPLGA 90° scaffold-tissue samples removed after 35 days in vivo.

DETAILED DESCRIPTION

Figures 5A, 5B:
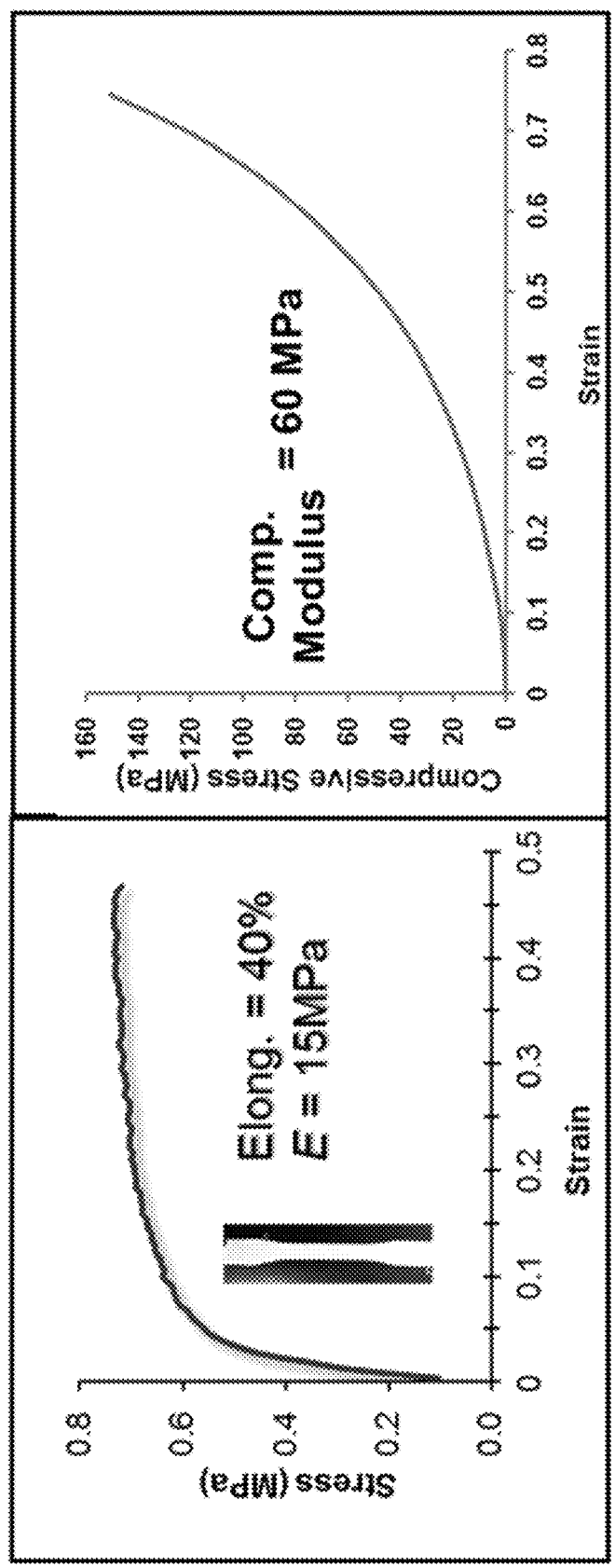
FIG. 5(A). Tensile mechanical testing results for bulk 90 wt. % HAPCL composites.
FIG. 5(B). Compressive mechanical testing results for bulk 90 wt. % HAPLC composites.

Ink formulations comprising bioactive particles, methods of printing the inks into three-dimensional (3D) structures, and methods of making the inks are provided. Also provided are tissue growth scaffolds made from the inks, methods of forming the tissue growth scaffolds using 3D printing techniques, and methods for growing tissue on the tissue growth scaffolds.

The inks comprise a plurality of bioactive ceramic particles, a biocompatible polymer binder, and at least one solvent. In addition the inks may comprise other additives, including at least one bioactive factor (e.g., genes, proteins, peptides, growth factors, pharmaceutical compounds, antibiotics and the like that facilitate tissue growth by, for example, inducing cell differentiation), and plasticizers.

Unlike other high HAp-content biomaterials, which are brittle, require high temperature processing, and have limited bioactivity, high HAp-content biomaterials printed from the present inks can be hyperelastic, and may be quickly fabricated at room temperature into complex, implantable structures using an extrusion-based 3D-printing platform. Structures as small as 1 $mm^3$ or as large as many $cm^3$ can be fabricated and manipulated post printing via rolling, folding, cutting, or fusing with other pre-formed structures. The hyperelastic structures may be cyclically compressed and return to their net original form after unloading. These properties may be attributed to the presence of elastomeric polymer binders, along with a characteristic porous microstructure resulting from the specific ink formulation and 3D printing process. The microstructure not only permits rigid HAp particles to translate upon mechanical loading and return to their original position upon unloading, but it can also present a composition and nano- and micro-porosity biomimetic of natural osseus tissues.

As used herein, the term bioactive ceramic refers to a material which is capable of promoting the growth of new tissue, such as osteo, chondral or osteochondral tissue. In addition to comprising a bioactive material, the ceramic particles are desirably also relatively stiff, capable of promoting cell adhesion, and are osteoinductive, osteoconductive and/or chondrogenically active. Some embodiments of the bioactive ceramics support osteogenesis and chondrogenesis under specific differentiation media conditions. That is, they can be both chondrogenically and osteogenically active. Hydroxyapatite (HAp) is an example of a suitable bioactive ceramic from which the bioactive ceramic particles can be comprised. HAp is a bioactive ceramic and the native mineral component of natural bone. HAp has osteoconductive and osteoinductive properties, which provide it with the capacity to induce the growth of new, natural bone on and around the material, as well as biochemically promoting new bone formation. Calcium phosphates, such as tricalcium phosphate (TCP) are additional examples of bioactive ceramics that can be included in the ink compositions.

As used herein, the term biocompatible refers to a material that does not have a significant negative impact on tissue growth and viability. In addition to comprising a biocompatible material, the polymer binders are desirably also easy to process, elastic and biodegradable. The biocompatible polymer binder may also be a bioactive material. Examples of suitable polymer binders include biocompatible, bioactive polyesters, such as polylactic acid, polyglycolic acid, poly-lactic-co-glycolic acid (PLGA) (also referred to as polylactide-co-glycolide (PLG)), polycaprolactone (PCL) or any combination of these. PCL and PLGA are synthetically derived polyesters. They are elastic, degradable, can be used for cartilaginous tissue regeneration and have been shown to support stem cell differentiation down osteogenic and chondrogenic pathways. The biocompatibility of the inks and objects printed from the inks is demonstrated using in vivo and in vitro models in the examples below.

The use of elastic polymer binders, such as PCL and PLGA, promotes the robustness of objects, films and coatings formed from the ink compositions. In addition, when the ink compositions are extruded, the elastomeric binders provide for the formation of extruded stands that are continuous, flexible and strong. Moreover, 3D-structures that are extruded or 3D-printed from the ink compositions can adopt the elastomeric properties of the elastic polymer binders. Thus, some embodiments of objects that are formed from the ink compositions have hyperelastic mechanical properties, which allow them to 'bounce back' to their original shape after undergoing loading (e.g., compression or tension). In addition, sheets that are 3D-printed from the inks can be rolled, folded and cut.

The hyperelastic structures are comprised of incompressible solids capable of undergoing large degrees of elastic deformation and then returning to their original shape upon unloading. The examples illustrate hyperelastic 3D-printed objects made with HAPCL or HAPLGA inks. The hyperelastic objects rebounded to their original shape after being pulled, up to ~40%, or compressed upwards of 55%.

The regenerative capacities of the materials are not only dependent on the chemical properties of the materials, but are also affected by the mechanical properties of the materials. For example, stem cells will respond to a material's stiffness and behave accordingly. Thus, in those embodiments comprising HAp and PCL, HAp induces stem cells to primarily follow osteogenic differentiation pathways, while PCL induces stem cells to primarily follow chondrogenic differentiation pathways.

Because the inks can be formulated and printed at relatively low temperatures (e.g., room temperature; ~23° C.), bioactive factors, such as proteins, peptides, growth factors and genes, and/or pharmaceutical compounds can be added to the ink formulation and, subsequently incorporated into structures made from the inks, without undergoing heat-induced degradation. In addition, the low-temperature processing makes it possible to formulate inks having a high bioactive ceramic content. For example, some embodiments of the inks, and the structures made therefrom, have a bioactive ceramic content of at least 60 weight percent (i.e., a weight fraction of 0.6), based on the combined weight of the bioactive ceramic and the biocompatible polymer binder. This includes embodiments having a bioactive ceramic content of at least 70 weight percent based on the combined weight of the bioactive ceramic and the biocompatible polymer binder, at least 80 weight percent based on the combined weight of the bioactive ceramic and the biocompatible polymer binder and at least 90 weight percent based on the combined weight of the bioactive ceramic and the biocompatible polymer binder. Additionally, the ability to print at relatively low temperatures permits co-printing alongside temperature sensitive materials such as hydrogels and hydrogels containing living cells. This permits multi-material, living bone structures to be printed.

The inks can be made by dissolving a biocompatible polymer binder in a first solvent and mixing one or more bioactive factors into the solvent to form a solution; dispersing bioactive ceramic particles into a second solvent to form a dispersion; and mixing the solution and the dispersion to form the ink. The second solvent may be, for example, a graded solvent, as illustrated in the example, below. Excess solvent can then be evaporated from the resulting formulation to provide a more viscous mixture or "paste". This entire process can be carried out at low-temperatures, such as at room temperature—significantly lower than those typically used in a hot-melt based process. For example, in some embodiments, the methods of making the inks are carried out at a temperature of no greater than about 35° C. This includes embodiments of the methods that are carried out at about room temperature (e.g., in a temperature range from about 22 to about 26° C.).

The inks can be used to form a variety of structures using a variety of techniques. For example, the inks, including the inks in paste form, can be cast into a film or coating on a substrate or into a mold to create a 3D object. However, the inks are particularly well-suited for use as printable inks in 3D printing applications directed to the fabrication of bioactive scaffolds. Upon casting or printing, the remaining solvent can be fully evaporated, resulting in a solid structure. Organic solvent removal can be facilitated by washing the printed object in ethanol, followed by washing in sterile water. The resulting structure does not typically require any post-processing. The resulting composite material is hyperelastic and comprises a continuous, thin matrix of the binder in which the ceramic is dispersed. In those embodiments comprising PCL or PLGA and HAp, which are referred to herein as HAPCL composites and HAPLGA composites, respectively, the macro mechanical properties of the resulting material may be dominated by PCL or PLGA, while the micro mechanical and bioactive properties may be dominated by HAp.

Coatings, films, scaffolds and other structures made from the inks may be bioactive, biodegradable and characterized by a rough surface texture that promotes cell adhesion, proliferation and activity. In addition they may be characterized by a large elongation to break. As a result, the structures can be used in a variety of tissue engineering applications, including meniscal, cartilage, and subchondral bone replacement and regeneration (i.e. for osteoarthritis, cartilage defects, and damaged meniscal tissue); other cartilaginous tissues (i.e. ear, nose, esophagus, trachea); ligament-bone fixation devices for improving integration and restoring mechanical function after ligament repair surgery; craniofacial regenerative implants (e.g., skull plate, nose, cheek bone); support and regeneration of tissue following corrective surgeries treating cleft pallet; alveolar ridge support and regeneration immediately following or long after tooth removal; spine fusion and regeneration; regeneration in any long bones, hip bones, or bones in the extremities (i.e. hand, wrist, ankle, foot, toes); drug, gene, or growth factor delivery; and biodegradable implants or coatings.

In addition, the ink compositions are able to bond to previously deposited layers or separately printed object parts—including object parts that are themselves printed using the present 3D ink compositions. Therefore, two or more object parts can be fused together using the 3D ink compositions as a self-adhesive. In these applications, the ink compositions not only act as an adhesive, but also seamlessly meld the objects together at the location of deposition. As a result, extremely complex or very large 3D objects that could otherwise not be easily 3D printed directly can be created by seamlessly fusing parts together with the same ink composition that comprises the parts themselves.

For tissue engineering applications, the inks are desirably used to fabricate tissue growth scaffolds, which are porous structures that permit cell integration, tissue ingrowth, and vascularization. The porous scaffolds can be printed via layer-by-layer extrusion of an ink through a print head of a printer, such as a bioplotter (e.g., Envision TEC, GmbH), or through the needle of a syringe. The use of 3D printing for the fabrication of the scaffolds is advantageous because it provides for regular geometric patterning of the layers that make up the scaffold, which makes it possible to control and tailor the porosity, pore size and pore interconnectivity of the scaffold. For example, the printed layers may comprise a plurality of printed fibers. In some embodiments, the fibers in each layer are substantially parallel to one another, while the fibers in a given layer are not oriented parallel to the fibers in other layers. A schematic diagram showing the top view of such an embodiment is provided in FIG. 2D. The printing can be carried out at relatively low extrusion temperatures, including temperatures in the range from about room temperature (i.e., ~23° C.) to about 40° C.

The porous scaffolds can be used as tissue growth scaffolds by seeding the scaffolds with tissue-forming cells, or cells that are precursors to tissue-forming cells, within the pores of the scaffolds. Tissue can be grown by culturing the seeded scaffolds in a cell growth culture medium. Human mesenchymal stem cells, hematopoetic stem cells, embryonic stem cells, and induced pluripotent stem cells are examples of precursors to tissue-forming cells. Examples of tissue-forming cells include osteoblasts, chondrocytes, fibroblasts, endothelial cells, and myocytes. Because bioactive factors can be incorporated directed into the scaffold as it is fabricated, there is no need to incorporate bioactive factors into the culture medium. Thus, in some embodiments, the tissue growth is carried out in a culture medium that is free of bioactive factors that promote the growth of the tissue.

EXAMPLES

The following examples illustrate the use of the present high HAp content inks to form a 3D-printable biomaterial, Hyperelastic Bone (HB), comprised of 90 wt. % hydroxyapatite (HAp) ceramic particles and 10 wt. % biocompatible elastomer.

Briefly, in vitro studies using human mesenchymal stem cells, described below, reveal that HB is highly supportive of cellular activity. Seeded stem cells readily proliferate to quickly coat all available surfaces and fill the inter-scaffold pore volume. HB is also inherently osteoinductive, promoting osteogenic differentiation of stem cells, including extracellular matrix (ECM) deposition and de novo mineralization without the need for additional osteogenic chemical or mechanical factors. Histological and electron microscopy imaging of subcutaneously implanted HB scaffolds in a mouse model, compared to hot-melt 3D-printed HA-polymer scaffolds, reveal that host tissue more readily integrates within and vascularizes throughout the HB scaffolds without any observable host immune response. 3D-printed hyperelastic bone's unique mechanical and biological properties, combined with the ease of fabrication, potential for scalability, and low material and processing costs make this material system a very promising new osteogenic bone substitute for orthopaedic, dental, and craniofacial tissue regeneration applications.

Example 1

This example describes the room temperature synthesis of a castable and 3D-printable HAp-dominant HAPCL composite material comprised of micron or nano-scale HAp particles bound together with a thin, percolating network of biocompatible, elastic PCL (FIG. 1). The resulting material has the following properties: rough surface dominated by exposed HAp particles; macro mechanical properties dominated by PCL (elastic, large elongation to break); micro mechanical properties dominated by HAp particles; biodegradable; osteoinductive; and easy to form into complex, porous scaffold architectures.

Materials and Methods

All processes were performed at room temperature in atmosphere unless otherwise noted. The desired weight percent (wt. %) of HAp relative to PCL of the final structure was first determined (e.g. 90 wt. % HAp=9 g HAp to 1 g PCL). 9 g HAp (micro or nano-scale) was suspended in a mixture of dichloromethane, 2-butoxyethanol, and dibutyl phthalate at respective mass ratios of 8:2:1. The HAp suspension was then sonicated for at least 1 hour. Separately, 1 g of PCL was fully dissolved in 6 g dichloromethane. If bioactive factors were incorporated, these factors were added in the 6 g dichloromethane prior to addition of PCL. Once fully dissolved, the PCL solution should be viscous but will still flow under its own weight. The HA-graded solvent suspension was then added to the PCL solution, physically mixed for several minutes and sonicated for at least one hour. This process ensured that all HAp particles were dispersed and coated with solubilized PCL and bioactive factors. If casting the material, it should be cast into the mold or container of interest at this point. Excess solvent was permitted to evaporate overnight or until the material was dry. If the intended end use is 3D printing, excess solvent is evaporated until the HAPCL ink attains a viscosity of approximately 25 Pa·s. The evaporation rate can be increased by sonicating the mixture at 40° C.

Figure 16:
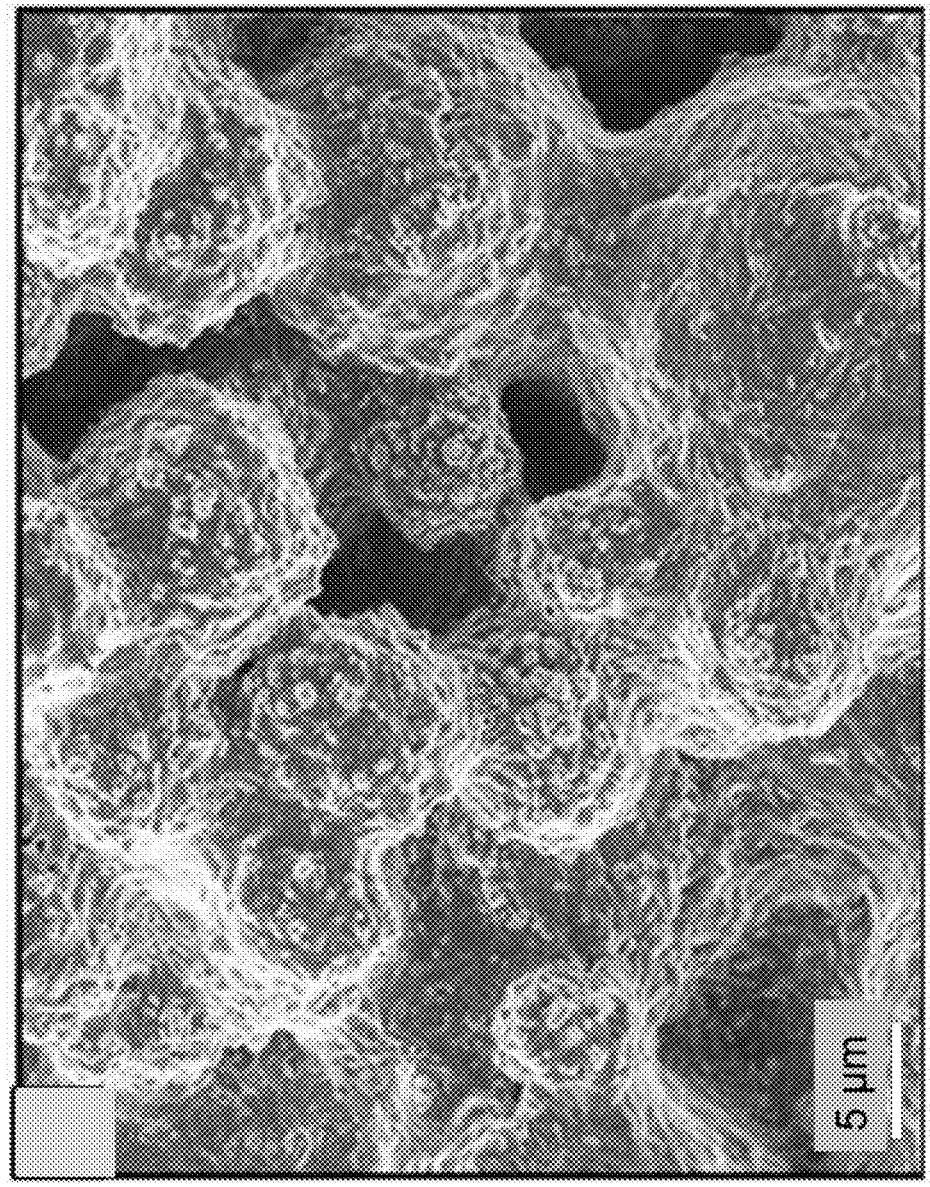
FIG. 16. SEM micrograph of HAPCL fiber microstructures, wherein the fiber was printed from an ink composition comprising a graded solvent. Scale bar 5 μm.

At this point, the mixture was added to a 3D printer extrusion cartridge. For the purposes of this work, an EnvisionTec Gmbh 3D-Biopotter® (Germany) was used. FIG. 16 is an SEM micrograph of HAPCL fiber microstructure. The material was then fashioned into designer, porous 3D objects via layer-by-layer extrusion (shown schematically in FIG. 2A) from a conical 200 μm-diameter polyethylene nozzle at 6.2 bar pressure and 4 mm/s speed or from a conical 400 μm polyethylene nozzle tip 4 bar pressure and 8 mm/s. Top and side views of printed structures are shown in FIGS. 2B and 2C, respectively. Other larger nozzle diameters may be used, but only two are described for the purposes of this example. The material was extruded onto PTFE coated substrates, which were placed on ice after printing to lift the printed structures. (Many other polymeric and non-polymeric substrates, such as sandpaper, could also be used.) Due to the high vapor pressure of the solvents, and small volume of extruded material, the HAPCL strands immediately dried upon deposition onto the substrate. Examples of printed scaffold structures are shown in the images in FIG. 3 and SEM micrographs in FIG. 4. FIG. 3A shows an 8-layer 30° advancing angle structure and FIG. 3B shows an 8-layer 90° advancing angle structure with a 250 μm offset every other layer. In FIG. 4, the spherical objects are HAp particles, and the smooth material between particles is PCL. In FIG. 4A, the printed fibers are non-linear along their longitudinal axes. FIG. 4C is a cross-sectional view of the scaffold of FIG. 4A. In FIG. 4B the fibers in each layer are oriented substantially parallel, while the fibers in adjacent layers are oriented substantially perpendicular. FIG. 4D is a cross-sectional view of the scaffold of FIG. 4B. If the scaffold objects are intended for in vitro use with living cells or in vivo work with animals or human patients, they are first submerged in sterilized deionized water for at least three days to remove organic residues.

Mechanical Characterization:

A 90 wt. % HAp HAPCL solution was cast into PTFE coated petri dishes and permitted to dry. Flat tensile specimens with 20 cm gauge length and 2.2 mm thickness were loaded at an extrusion rate of 1 mm/min. The resulting tensile properties are displayed in FIG. 5A and indicate a tensile modulus of 15±4.1 MPa and average elongation at break of 40%. These values are much more similar to PCL than to HA. Compression tests were conducted on solid, 6 mm-diameter, 3 mm-thick disks. The results are shown in FIG. 5B. The compressive modulus was evaluated at 15% strain to be 60 MPa.

Incorporation of Bioactive Factors:

To demonstrate that bioactive factors could be successfully incorporated within the material and remain functional during the fabrication process, green fluorescent protein (GFP) was added to the PCL solution (5 μg GFP/1 g DCM). The synthesis procedure continued as described above and the material was printed into a porous scaffold form and imaged under black light. Conservation of GFP activity was evidenced by the green fluorescence from the GFP incorporated sample.

Figure 8B:
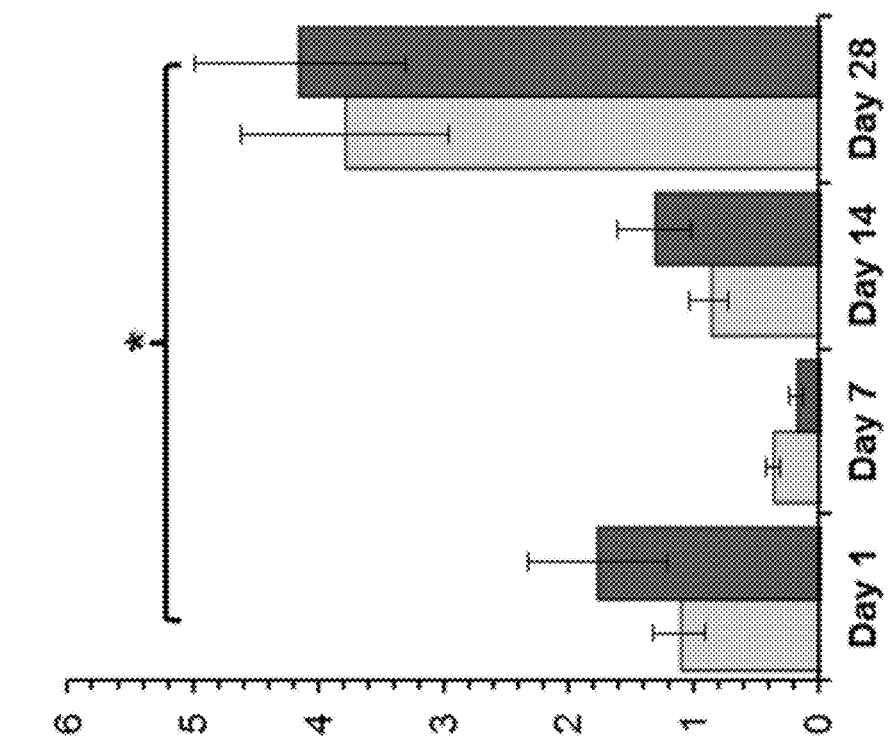
FIG. 8(B) corresponding normalized alkaline phosphatase activity (ALP) 7, 14, and 28 days after seeding.
Figure 8A:
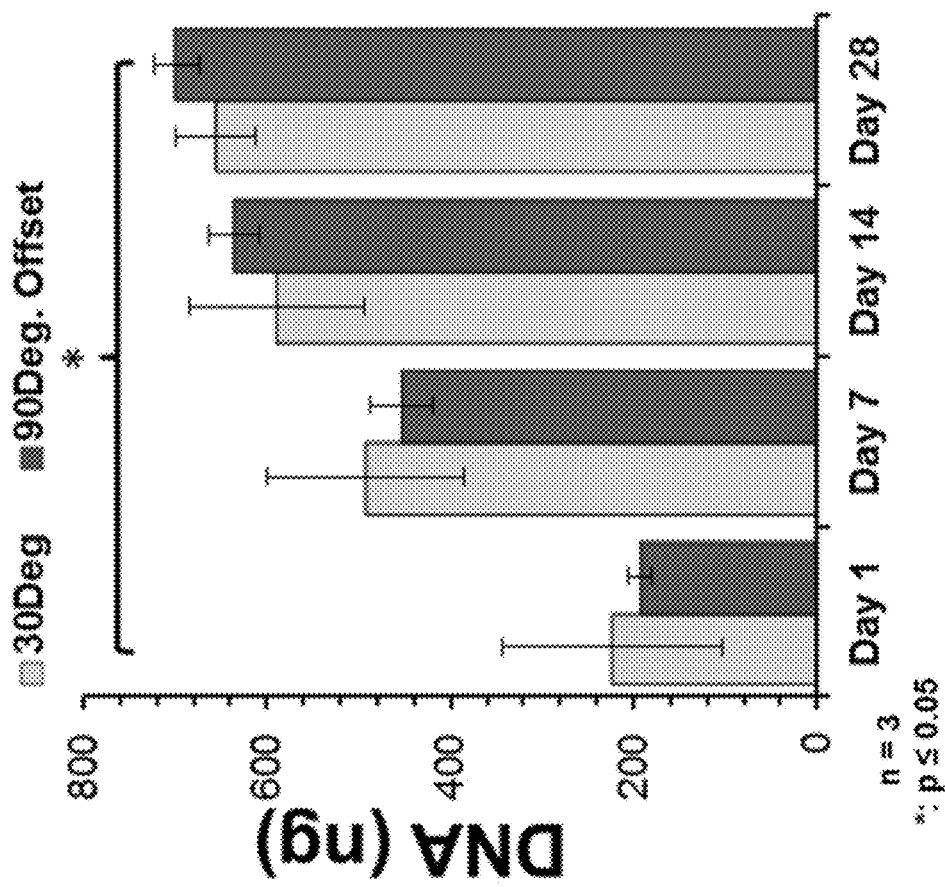
FIG. 8(A). DNA quantification of hMSCs seeded on 3D-bioplotted 30° HAPCL and 90° offset HAPCL.
Figures 12A, 12B, 12C:
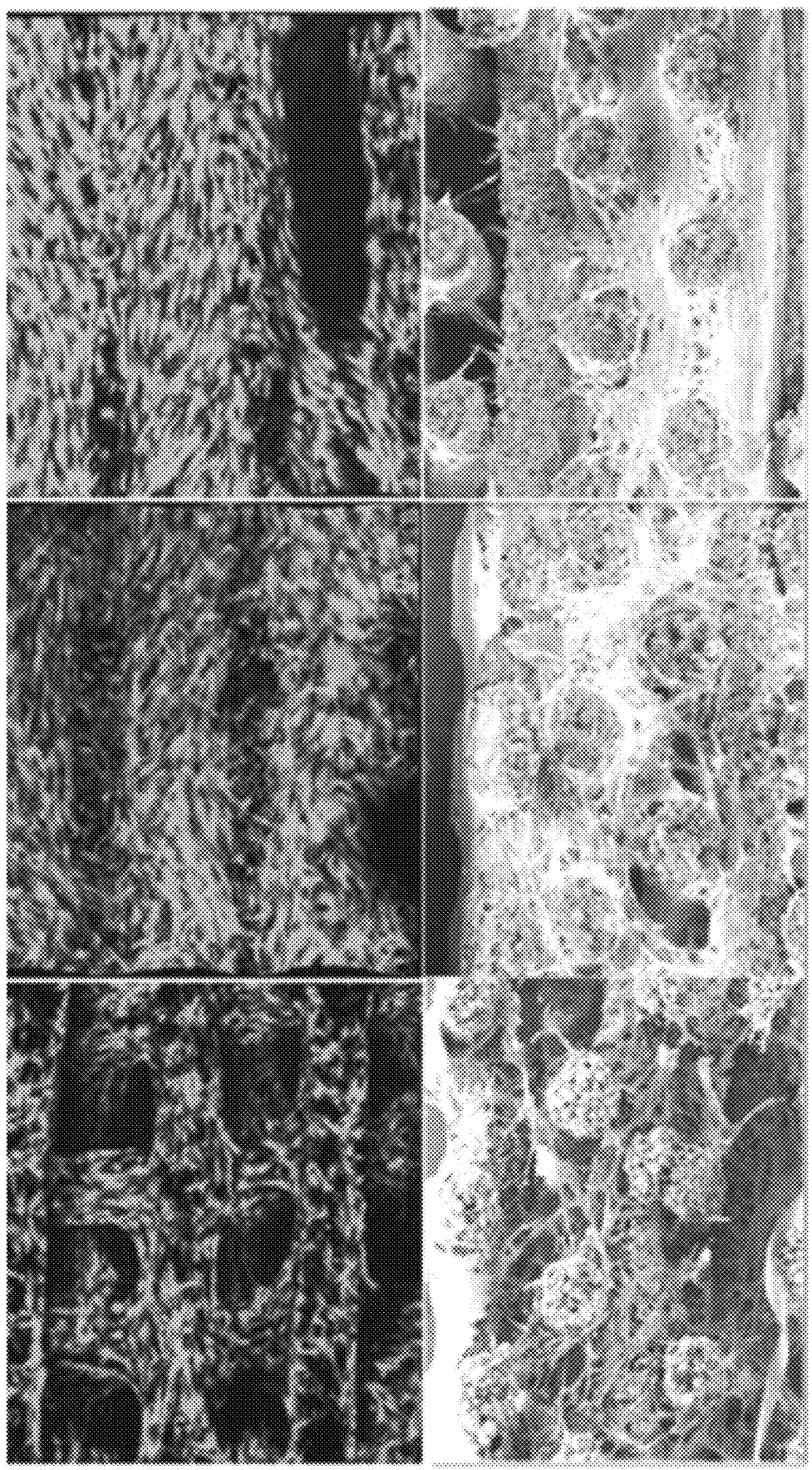
FIG. 12(A). Laser scanning fluorescent confocal microscopy live/dead reconstructions (upper panel) and corresponding cross-sectional SEM images (lower panel) of hMSCs on 90° offset HAPCL 7 days after seeding.
FIG. 12(B) Laser scanning fluorescent confocal microscopy live/dead reconstructions (upper panel) and corresponding cross-sectional SEM images (lower panel) of hMSCs on 90° offset HAPCL 14 days after seeding.
FIG. 12(C) Laser scanning fluorescent confocal microscopy live/dead reconstructions (upper panel) and corresponding cross-sectional SEM images (lower panel) of hMSCs on 90° offset HAPCL 28 days after seeding. Note: Bright areas=Live cells.

In Vitro Biocompatibility and Osteogenic Potential:

To ensure that the HAPCL synthesis, fabrication, and washing process left the material with no harmful organic residues, as well as to measure the material's biocompatibility and osteogenic potential, in vitro cell studies using human mesenchymal cells (hMSCs) on 3D-printed 90 wt. % HAp scaffolds with 200 μm pores were performed. The results of these studies at multiple time points are shown in the figures: FIG. 6—Laser scanning fluorescent confocal microscopy live/dead reconstructions of hMSCs 7 days after seeding on 30° offset HAPCL (FIG. 6A) and 90° offset HAPCL (FIG. 6B) (Bright Areas=Live Cells); FIG. 7—SEM of hMSCs 7 days after seeding on: (A) 30° HAPCL and (B) 90° offset HAPCL (hMSCs successfully adhere to and produce extra cellular matrix); FIG. 8—(A). DNA quantification of hMSCs seeded on 3D-bioplotted 30° HAPCL and 90° offset HAPCL and (B) corresponding normalized alkaline phosphatase activity (ALP) 7, 14, and 28 days after seeding (cell number increases over 4 weeks and ALP activity is significantly higher at 28 days after seeding); and FIG. 9—hMSC expression of osteogenic relevant genes on 3D-Bioplotted 30° HAPCL and 90° offset HAPCL at 7, 14, and 28 days after seeding in simple proliferation media, not a osteogenic differentiation media. Expression of osteogenic relevant genes increases significantly over the course of 28 days indicating successful osteogenic differentiation of the MSCs due to interaction with the HAPCL scaffold. Laser scanning fluorescent confocal microscopy images of live/dead reconstructions and corresponding cross-sectional SEM images of hMSCs on 90° offset HAPCL at day 7, day 14 and day 28, are shown in FIGS. 12A, 12B and 12C, respectively.

Figure 10A:
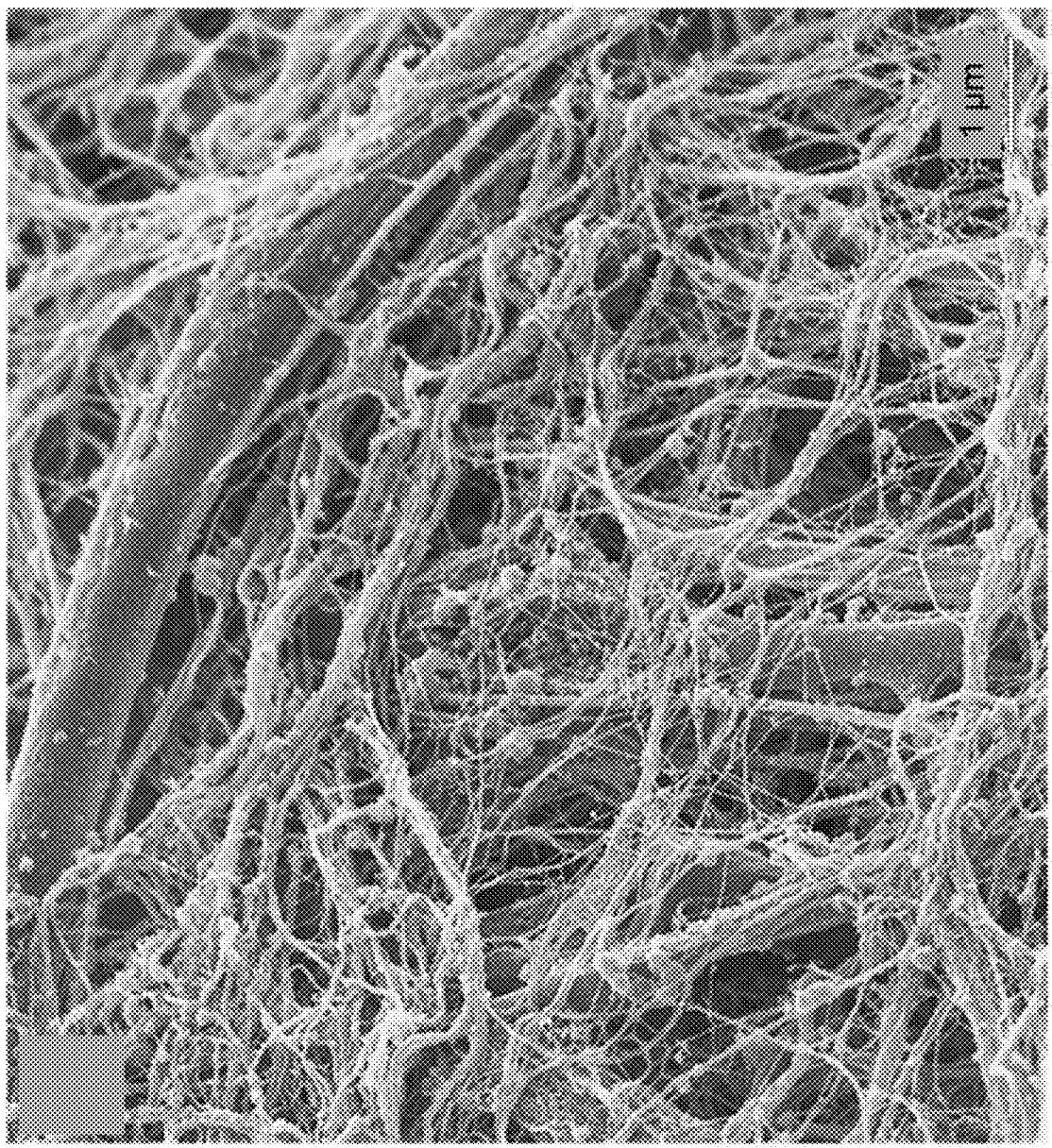
FIG. 10(A). SEM image of collagen synthesis and deposition by hMSCs on HAPCL scaffolds.
Figure 10B:
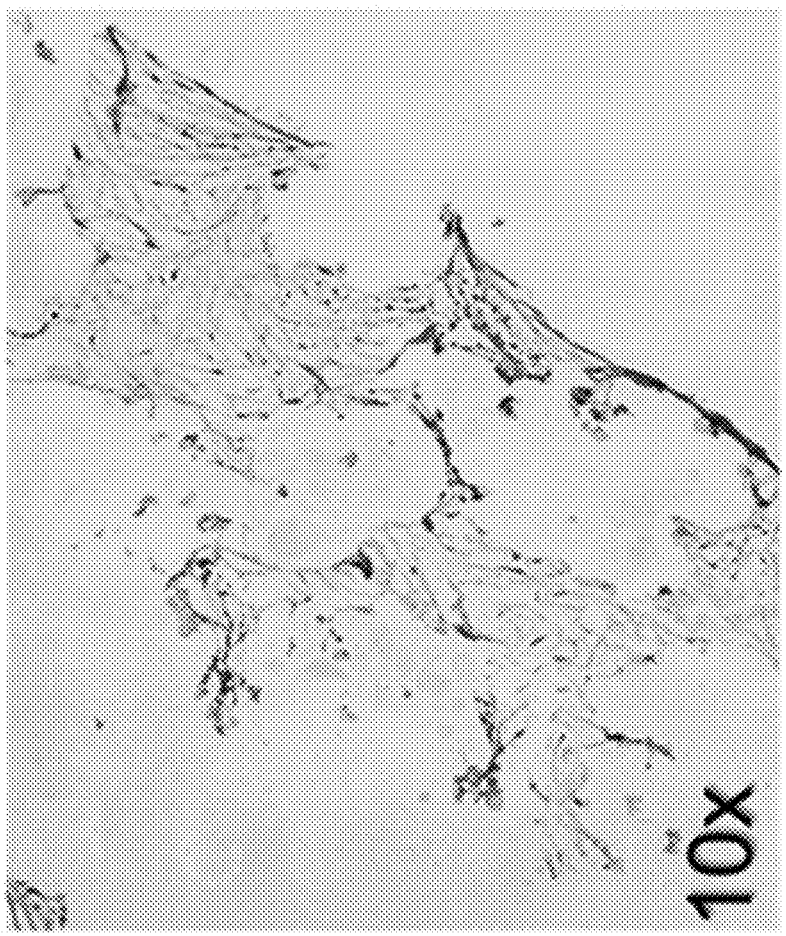
FIG. 10(B) histological image of collagen synthesis and deposition by hMSCs on HAPCL scaffolds.
Figures 11A, 11B:
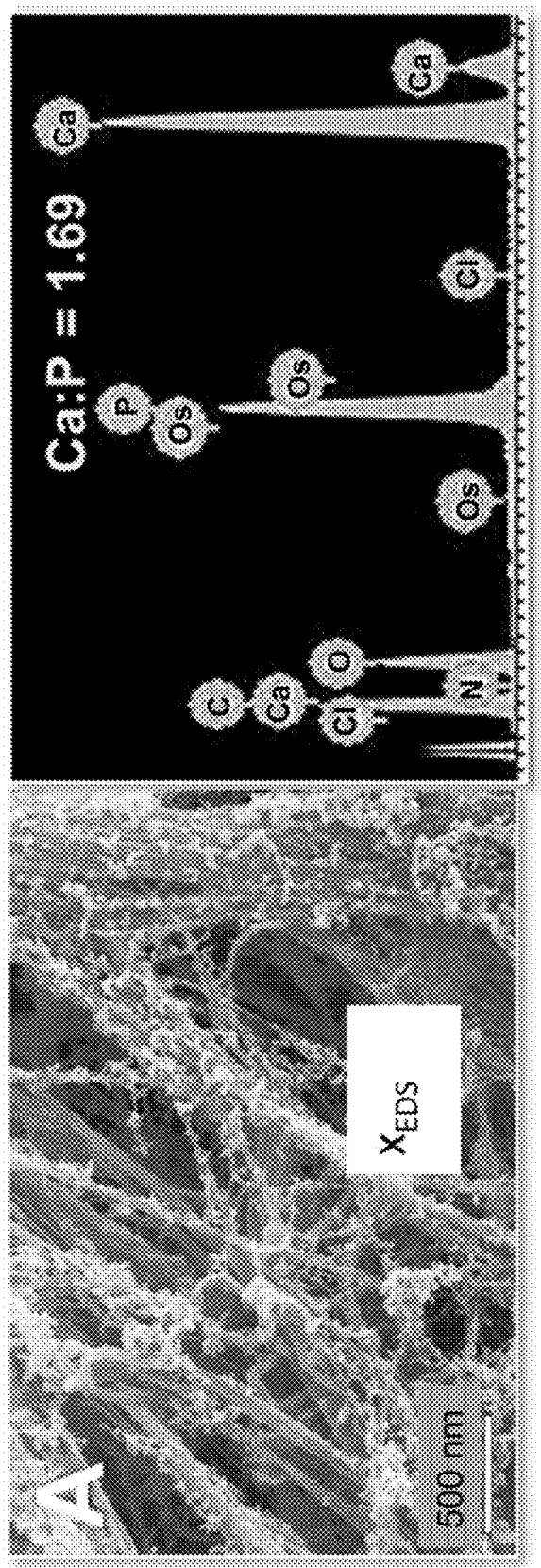
FIG. 11(A). SEM image of hydroxyapatite synthesis and deposition by hMSCs 28 days after seeding.
FIG. 11(B) corresponding energy dispersive x-ray spectrum of deposited mineral.

The utility of the scaffolds is further illustrated by the results shown in FIG. 10 and FIG. 11. FIG. 10 shows the collagen synthesis and deposition by hMSCs on HAPCL scaffolds as shown in: (A) SEM; and (B) histological images. hMSCs actively lay down collagen and other extra cellular matrix elements in HAPCL. FIG. 11 shows hydroxyapatite synthesis and deposition by hMSCs 28 days after seeding as shown in: (A) SEM; and (B) corresponding energy dispersive x-ray spectrum of deposited mineral. hMSCs actively synthesize and deposit hydroxyapatite (calcium to phosphate ratio 1.69) in HAPCL. Natural hydroxyapatite found in bone is 1.67. The HAp used in scaffold fabrication is 1.59. Cells in HAPCL produce HAp that is more natural than the original scaffold. Each of these results indicate that stem cells on the HAPCL material were viable, proliferate, actively produce extracellular matrix, and were undergoing osteogenic differentiation.

Example 2

This example describes the room temperature synthesis of a castable and 3D-printable HAp-dominant HAPLGA composite material comprised of micron or nano-scale HAp particles bound together with a thin, percolating network of biocompatible, elastic PLGA. The resulting material has the following properties: rough surface dominated by exposed HAp particles; macro mechanical properties dominated by PLGA (elastic, large elongation to break); micro mechanical properties dominated by HAp particles; biodegradable; osteoinductive; and easy to form into complex, porous scaffold architectures. Using in vivo subcutaneous implant testing on mice, this example demonstrates that the resulting printed material is biocompatible with no evidence of acute or chronic immune response. The promotion of vascularization by the material is also demonstrated using in vivo animal models.

Materials and Methods

All processes were performed at room temperature in atmosphere unless otherwise noted. The desired weight percent (wt. %) of HAp relative to PLGA of the final structure was first determined (e.g. 90 wt. % HAp=9 g HAp to 1 g PLGA). 9 g HAp (micro or nano-scale) was suspended in a mixture of dichloromethane, 2-butoxyethanol, and dibutyl phthalate at respective mass ratios of 8:2:1. The HAp suspension was then sonicated for at least 1 hour. Separately, 1 g of PLGA was fully dissolved in 6 g dichloromethane. If bioactive factors were incorporated, these factors were first dissolved in the 6 g dichloromethane prior to addition of PCL. Once fully dissolved, the PLGA solution should be viscous but will still flow under its own weight. The HA-graded solvent suspension was then added to the PLGA solution, physically mixed for several minutes and sonicated for at least one hour. This process ensured that all HAp particles were dispersed and coated with solubilized PLGA and bioactive factors. If casting the material, it should be cast into the mold or container of interest at this point. Excess solvent was permitted to evaporate overnight or until the material was dry. If the intended end use is 3D printing, excess solvent is evaporated until the HAPLGA ink attains a viscosity of approximately 25 Pa·s. The evaporation rate can be increased by sonicating the mixture at 40° C. At this point, the mixture was added to a 3D printer extrusion cartridge. For the purposes of this work, an EnvisionTec Gmbh 3D-Biopotter® (Germany) was used. The material was then fashioned into designer, porous 3D objects via layer-by-layer extrusion from a conical 200 μm-diameter polyethylene nozzle at 6.2 bar pressure and 4 mm/s speed or from a conical 400 μm polyethylene nozzle tip 4 bar pressure and 8 mm/s. Other larger nozzle diameters may be used, but only two are described for the purposes of this example. The material was extruded onto PTFE coated substrates, which were placed on ice after printing to lift the printed structures. Due to the high vapor pressure of the solvents, and small volume of extruded material, the HAPLGA strands immediately dried upon deposition onto the substrate.

Residual solvents and residues were removed from the 3D-printed HAPLGA composites following washes in 70% ethanol followed by several rinses in sterile water or phosphate buffered saline. Thermogravimetric analysis (TGA) of the HAPLGA scaffolds pre- and post-washing was used to determine if residual solvents were completely removed from the material prior to application in an in vitro or in vivo environment. As-printed scaffolds contain as much as 18 wt. % solvent. A 1 hour rinse in DI water left approximately 9 wt. % solvents. If rinsed in 70% ethanol (EtOH) followed by a water rinse, all residual solvents were removed from the material. Note: that also verified that HAPLGA was 90 wt. % HAp.

Figures 14A, 14B, 14C, 14D:
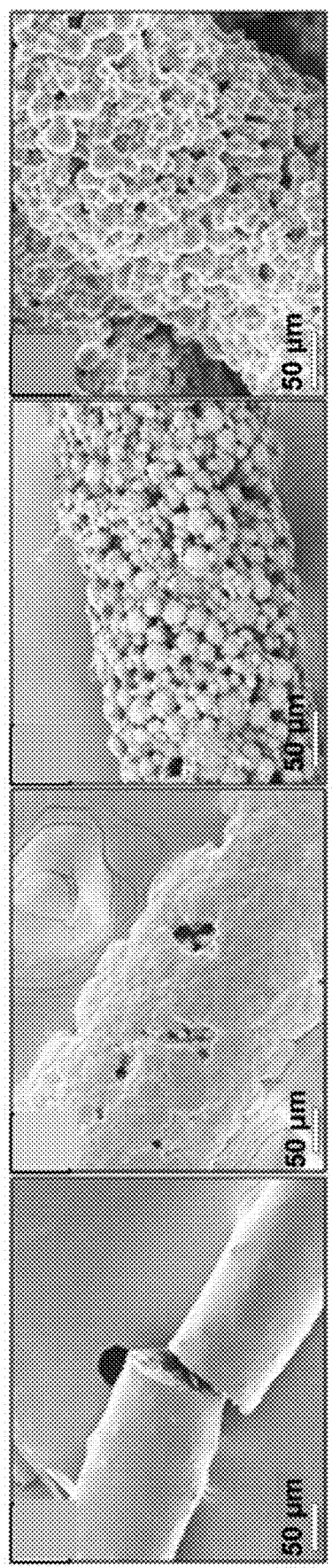
FIG. 14(A). SEM micrographs of representative fibers produced from high temperature-printed (hot melt) 25 vol. % (50 wt. %) HAp+PLGA (25-HT).
FIG. 14(B). SEM micrographs of representative fibers produced from room temperature-printed 25 vol. % (50 wt. %) HAp+PLGA (25-RT).
FIG. 14(C). SEM micrographs of representative fibers produced from room temperature-printed dichloromethane (DCM)-only 75 vol. % (90 wt. %) hydroxyapatite HAp+PLGA.
FIG. 14(D). SEM micrographs of representative fibers produced from HAPLGA. Scale bars 50 μm.

For comparison, fibers were also made via hot melt printing an ink composition comprising 25 vol. % (50 wt. %) HAp+75 vol. % (50 wt. %) PLGA. Fibers made from this ink composition are referred to herein as 25-HT fibers. The ink for the 25-HT fibers was formulated by mixing PLGA and HAp powder (1:1 by weight). This mixture was then loading into a Bioplotter high temperature cartridge, which was heated to 200° C. After 1 hour, the cartridge was maintained at 200° C. and the material was 3D-printed via extrusion. Solidification of extruded 25-HT fibers occurred due to melted polymer being exposed to room temperature and solidifying. The 25-HT fibers represent a common class of bioactive ceramic/polymer composites made by mixing a polymer binder and ceramic powders together, melting the polymer binder, and 3D printing via extrusion. Additional comparative fibers were made using an ink composition comprising 25 vol. % (50 wt. %) HAp++75 vol. % (50 wt. %) PLGA, which was processed into a room temperature printable ink in the same manner as the HAPLGA ink, except that the HAp and PLGA were combined is a ratio of 1:1 by weight, rather than a ratio of 9:1 by weight. Fibers made from this ink composition are referred to herein as 25-RT fibers. Finally, fibers were made from an ink comprising 75 vol. % (90 wt. %) HAp and 25 vol. % (10 wt. %) PLGA. This ink was formulated using the same procedure used to formulate the HAPLGA ink, except that a single solvent, DCM, was used rather than the mixed DCM, 2-butoxyethanol, and dibutylphthalate solvent used to formulate the HAPLGA ink. Fibers made from this ink composition are referred to herein as DCM-only fibers. FIG. 14 shows SEM micrographs of the fibers: FIG. 14A—25-HT fiber; FIG. 14B—25-RT fiber; and FIG. 14C—DCM-only fiber. FIG. 14D shows the HAPLGA fiber, respectively. FIG. 16 shows a magnified portion of the HAPLGA fiber of FIG. 14D.

Figure 15:
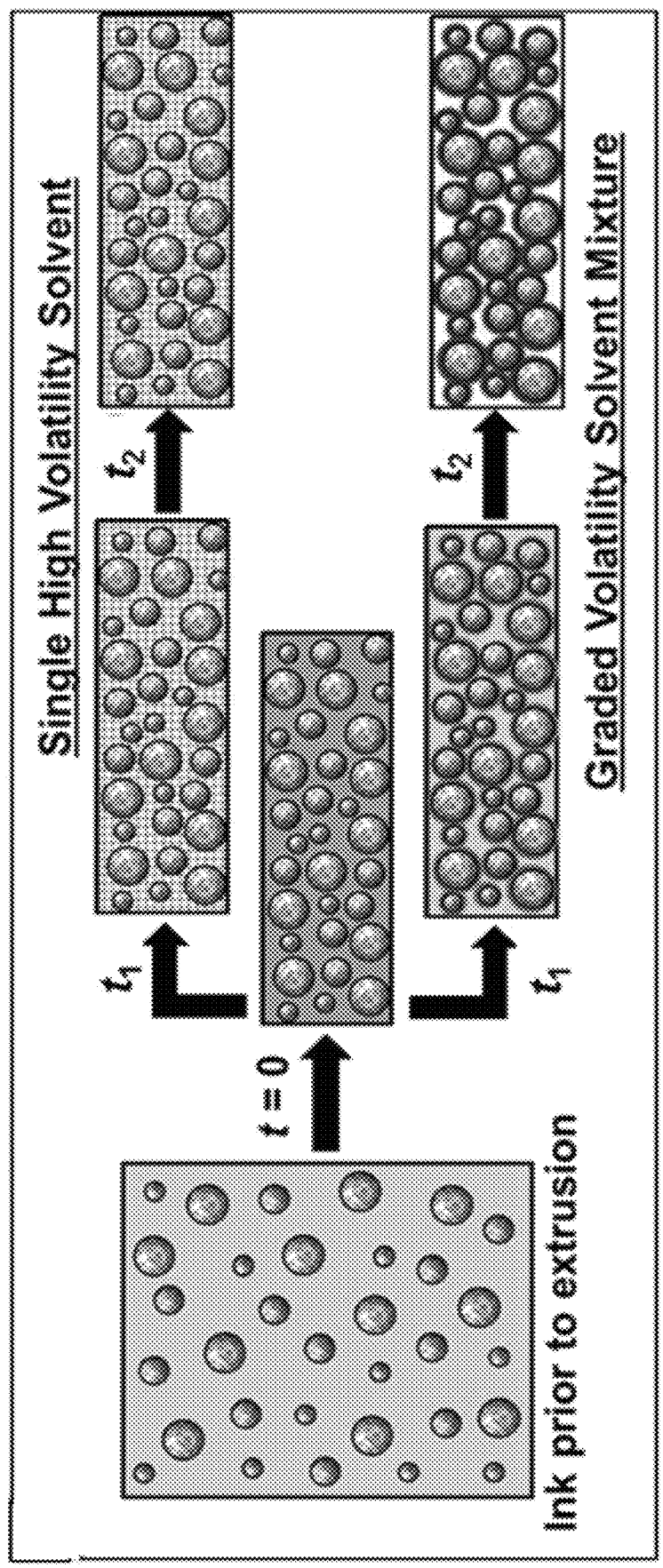
FIG. 15. Schematic representation of proposed HAPCL/HAPLGA and elastomer distribution within fibers using single or graded solvent mixture as a function of time after extrusion.

FIG. 15 shows a proposed mechanism that allows the inks to be 3D-printed and also formed into characteristic microstructures that are responsible for the bioactive and mechanical properties of the HAPLGA composites.

Figure 17:
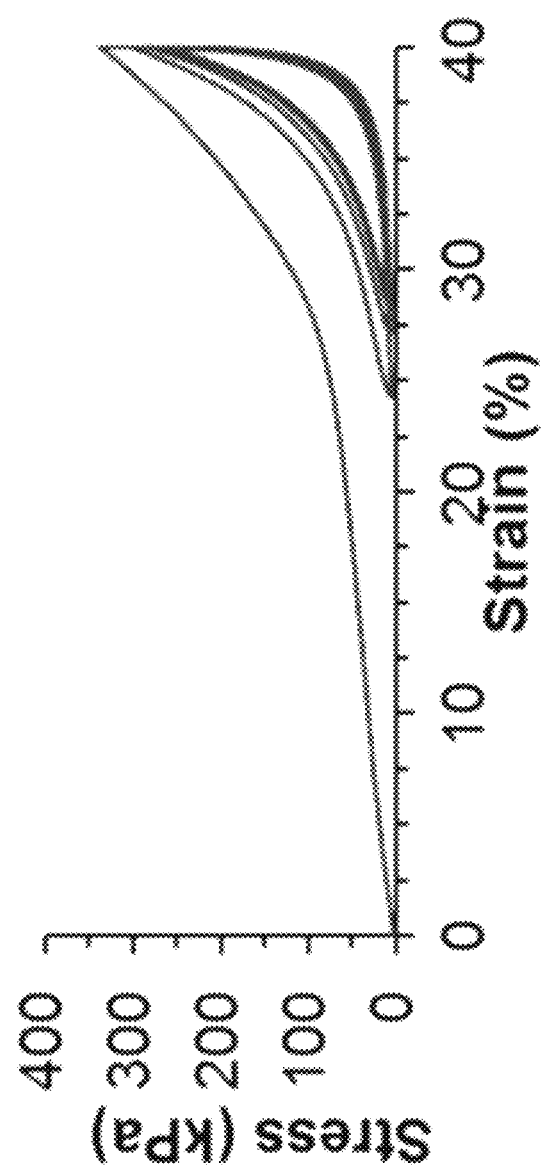
FIG. 17. Cyclic mechanical testing of a 3D-printed structure composed of the HAPLGA composite.
Figure 20:
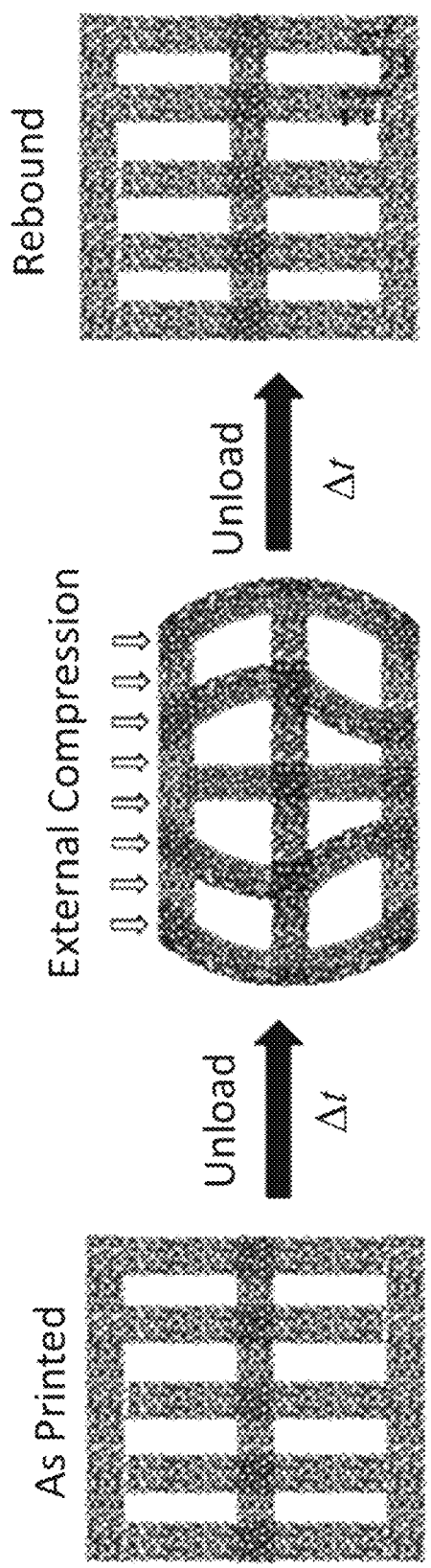
FIG. 20. Schematic illustration demonstrating that HAPCL and HAPLGA composites will exhibit superposed effects of compression, stretching and bending when loaded, but will rebound to their original architecture upon unloading over time.
Figure 21:
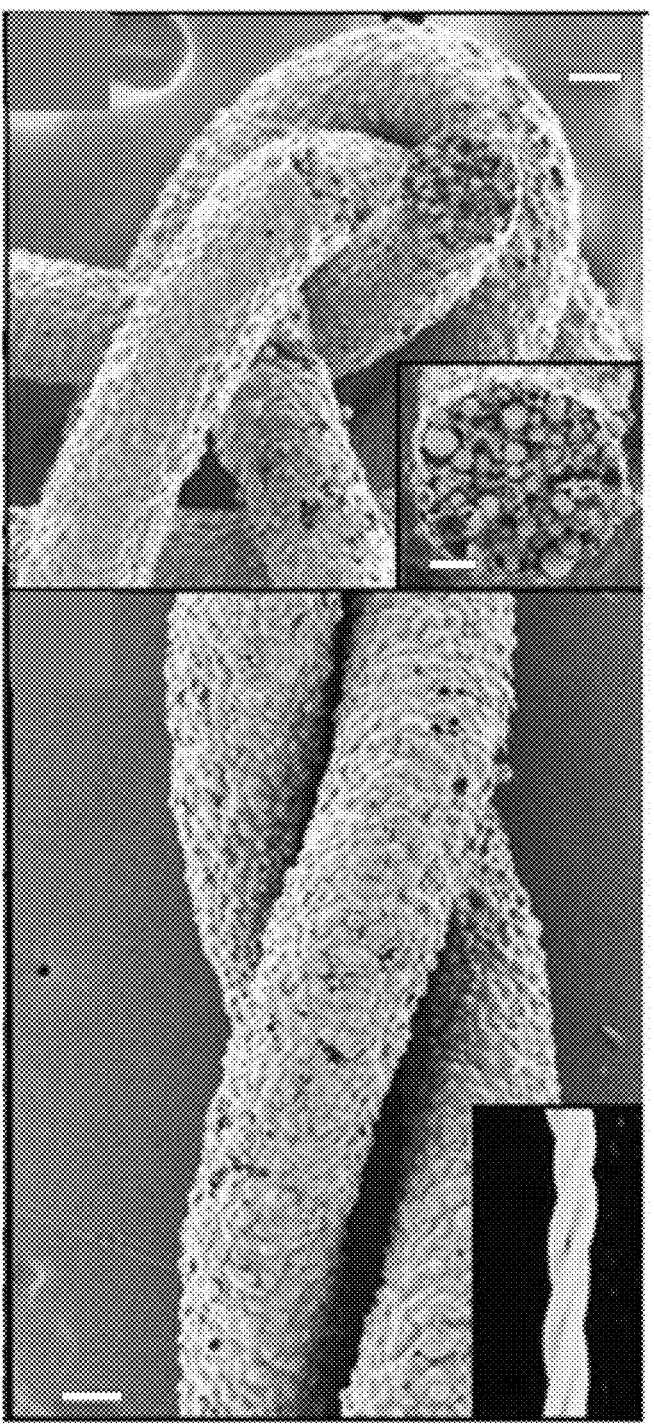
FIG. 21(A). SEM micrograph and photograph inset of HAPLGA hand-tied into a double micro-knot with inset showing fiber cross-section.
FIG. 21(B) SEM micrograph and photograph inset of HAPLGA formed into a twisted fiber cable. Scale bars 100 μm.

Characterization:

The 3D-printed HAPLGA structures were cyclically compressed more than 40% and returned to net original shape and strength upon unloading. The results of the testing are shown in FIG. 17. The hysteresis in the curve in FIG. 17 illustrates that upon compression and release, the HAPLGA composite material bounced back (demonstrating hyperelasticity) and was able to be loaded again. Ten cycles were using in this test. However, the hysteresis curves are so close to overlapping that the data for all 10 cycles cannot be individually distinguished.

FIG. 18 provides a schematic representation of the ceramic particle and elastomer distribution in: (A) an unloaded; (B) a compressed; (C) a stretched; and (D) a bent fiber. Arrows in the figures represent tensile and compressive loads. Upon unloading, a restoring force opposite in direction to the original tensile, compressive, or bending loads causes the fiber to return to its initial morphology, as shown in FIG. 19. As illustrated schematically in FIG. 20, the HAPLGA will exhibit superposed effects of compression, stretching and bending when loaded, but will rebound to their original architecture upon unloading over time.

FIG. 21A is an SEM micrograph of HAPLGA fibers hand-tied into a double micro-knot (the inset shows the fiber cross-section) and FIG. 21B is an SEM micrograph of HAPLGA fibers formed into a twisted fiber cable. Scale bars 100 μm.

Figure 22:
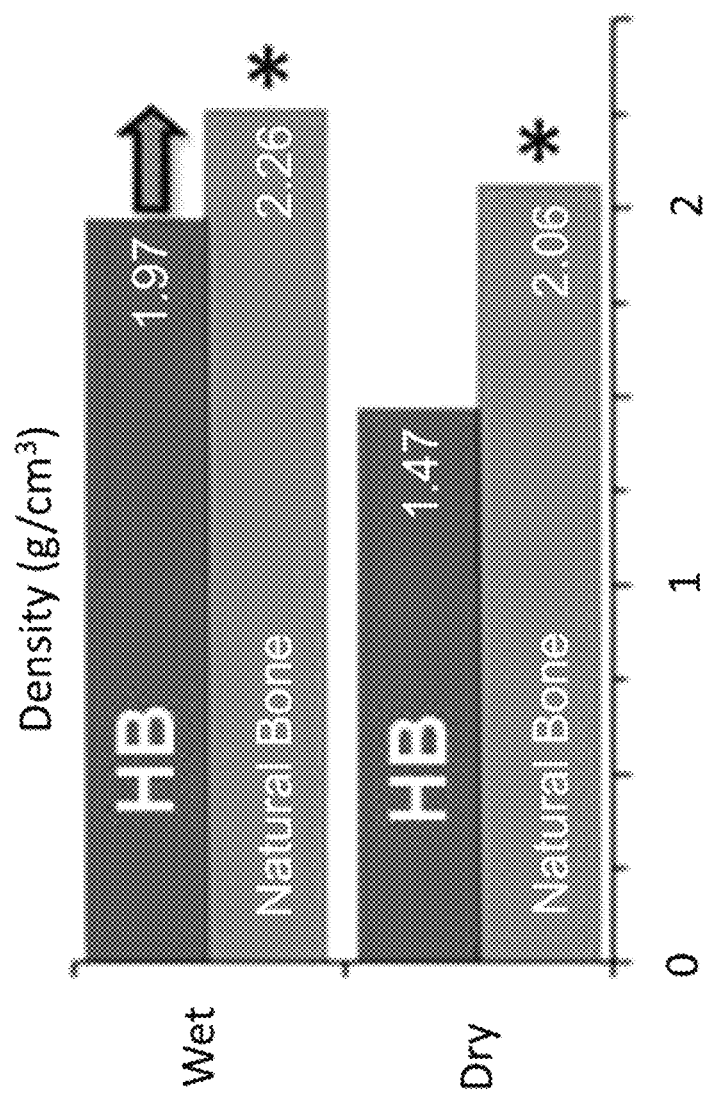
FIG. 22. Measured densities of dry and water saturated HAPCL fiber and (*) densities of dry and water saturated bone tissue from literature.

The densities of dry and water saturated HAPCL fibers and (*) densities of dry and water saturated bone tissue from literature were also measured and the results are shown in FIG. 22.

Figures 13A, 13B, 13C:
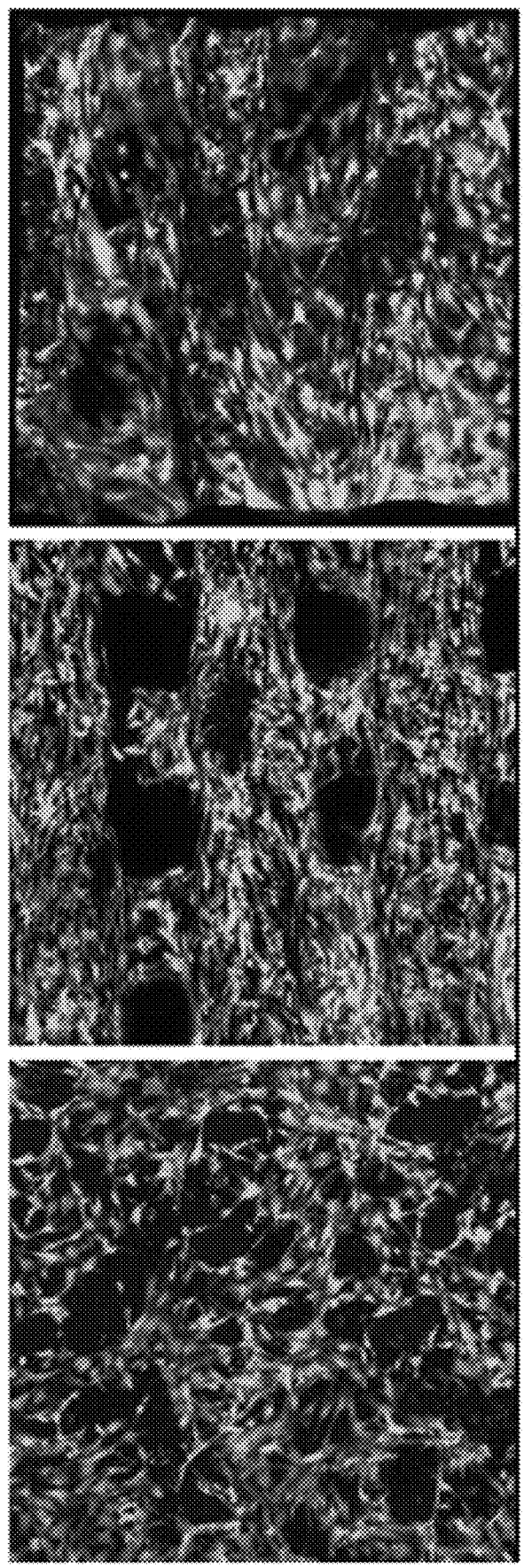
FIG. 13(A). Laser scanning fluorescent confocal microscopy live/dead reconstructions and corresponding cross-sectional SEM images of hMSCs on 90° offset HAPLGA 1 day after seeding.
FIG. 13(B) Laser scanning fluorescent confocal microscopy live/dead reconstructions and corresponding cross-sectional SEM images of hMSCs on 90° offset HAPLGA 7 days after seeding.
FIG. 13(C). Laser scanning fluorescent confocal microscopy live/dead reconstructions and corresponding cross-sectional SEM images of hMSCs on 90° offset HAPLGA 56 days after seeding. Note: Bright areas=Live cells.

In Vitro Biocompatibility and Osteogenic Potential:

To ensure that the HAPLGA synthesis, fabrication, and washing process left the material with no harmful organic residues, as well as to measure the material's biocompatibility and osteogenic potential, in vitro cell studies using human mesenchymal cells (hMSCs) on 3D-printed 90 wt. % HAp scaffolds with 200 μm pores were performed. Laser scanning fluorescent confocal microscopy images of live/dead reconstructions at day 1, day 7 and day 56, are shown in FIGS. 13A, 13B and 13C, respectively.

In Vivo Biocompatibility:

The 90° HAPLGA scaffolds were implanted subcutaneously (under the back skin) of BALB/c mice. Scaffolds were removed 7 or 35 days after implantation and observed using histology and SEM. No evidence of acute or chronic immune responses was found at either time point. It was also found that HAPLGA became highly vascularized and well integrated with the surrounding tissues. This confirmed the biocompatibility of HAPLGA as well as the potential for healthy tissue integration.

FIG. 23 shows SEM images of: (A) the entire scaffold cross-section, with incision site towards top of image; (B) a cross-section of representative blood vessels found throughout HAPLGA scaffold; (C) a magnified view of single HAPLGA strut cross-sections and surrounding tissues; and (D) a high-magnification image of HAPLGA strut-tissue interfaces and formed capillaries (arrow).

Figure 24A:
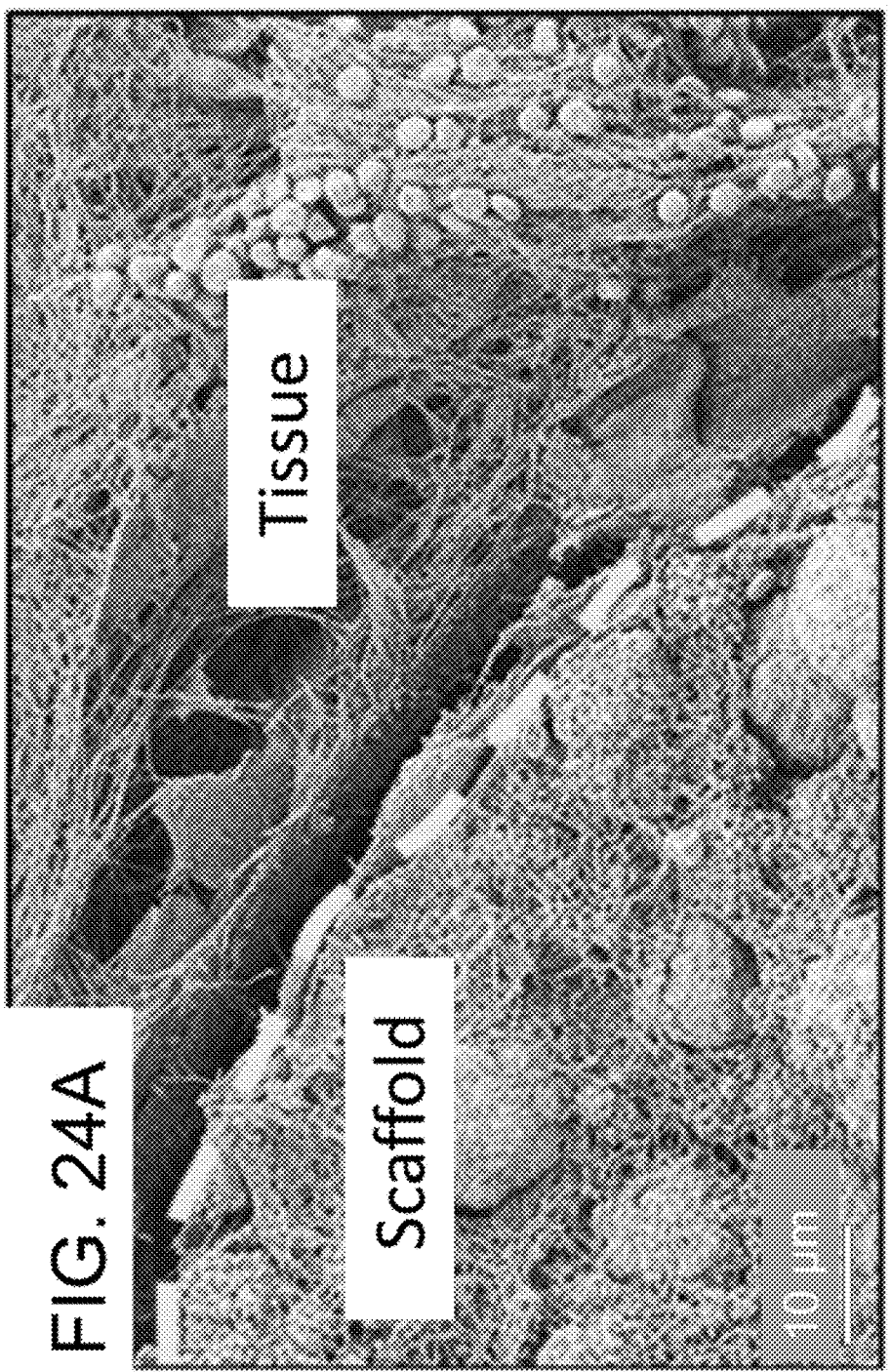
FIG. 24(A). SEM micrograph of explanted HAPLGA at a first magnification.
Figure 24B:
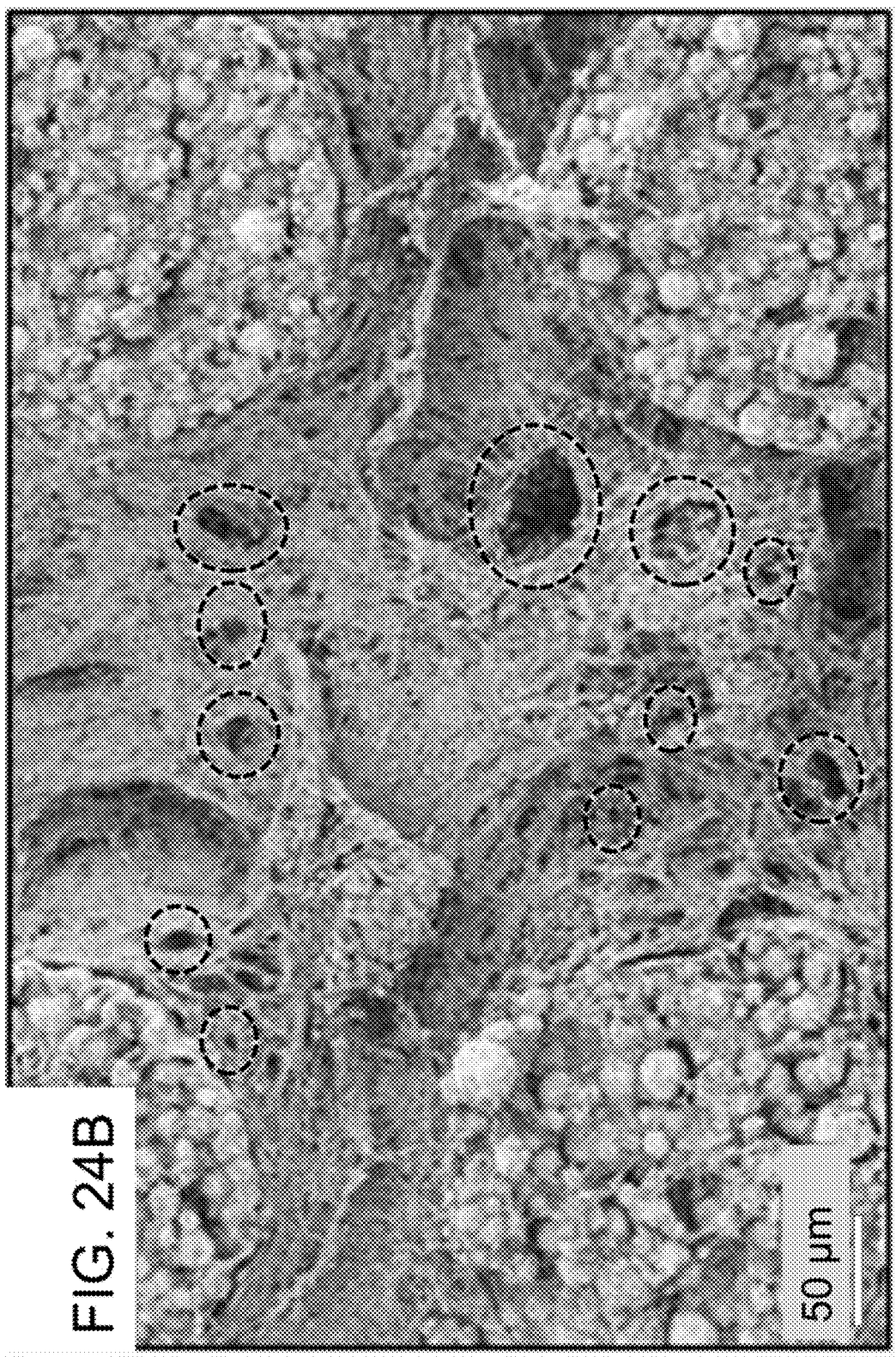
FIG. 24(B). SEM micrograph of explanted HAPLGA at a second magnification.
Figure 24C:
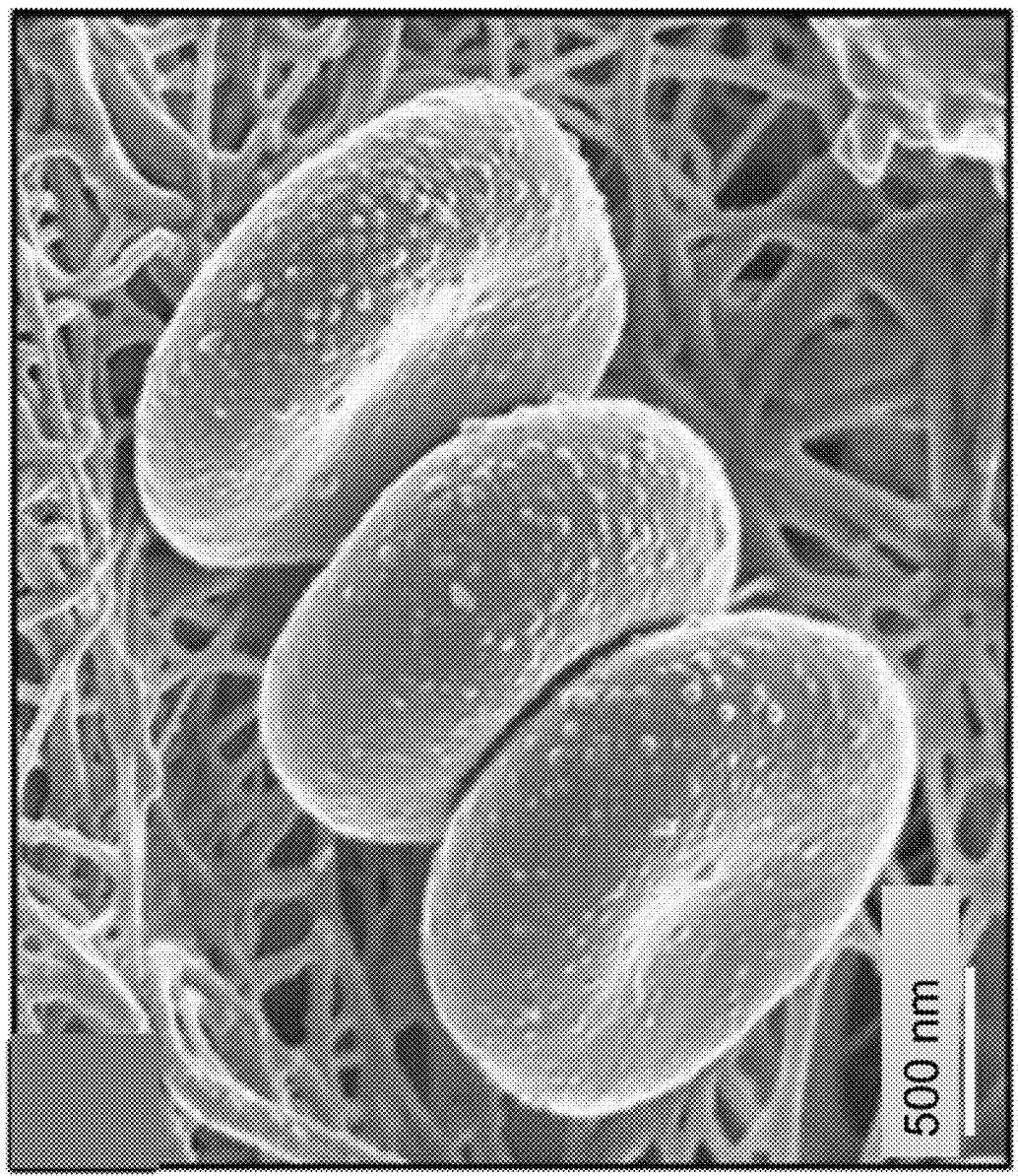
FIG. 24(C). SEM micrograph of explanted HAPLGA at a third magnification.
Figure 25A:
FIG. 25(A). SEM micrograph of a cross-sectional view of a single HAPLGA strut within the scaffold surrounded by in grown tissue and active vessels (arrow and circles) from explanted HAPLGA 90° scaffold-tissue samples removed after 35 days in vivo.
Figure 25C:
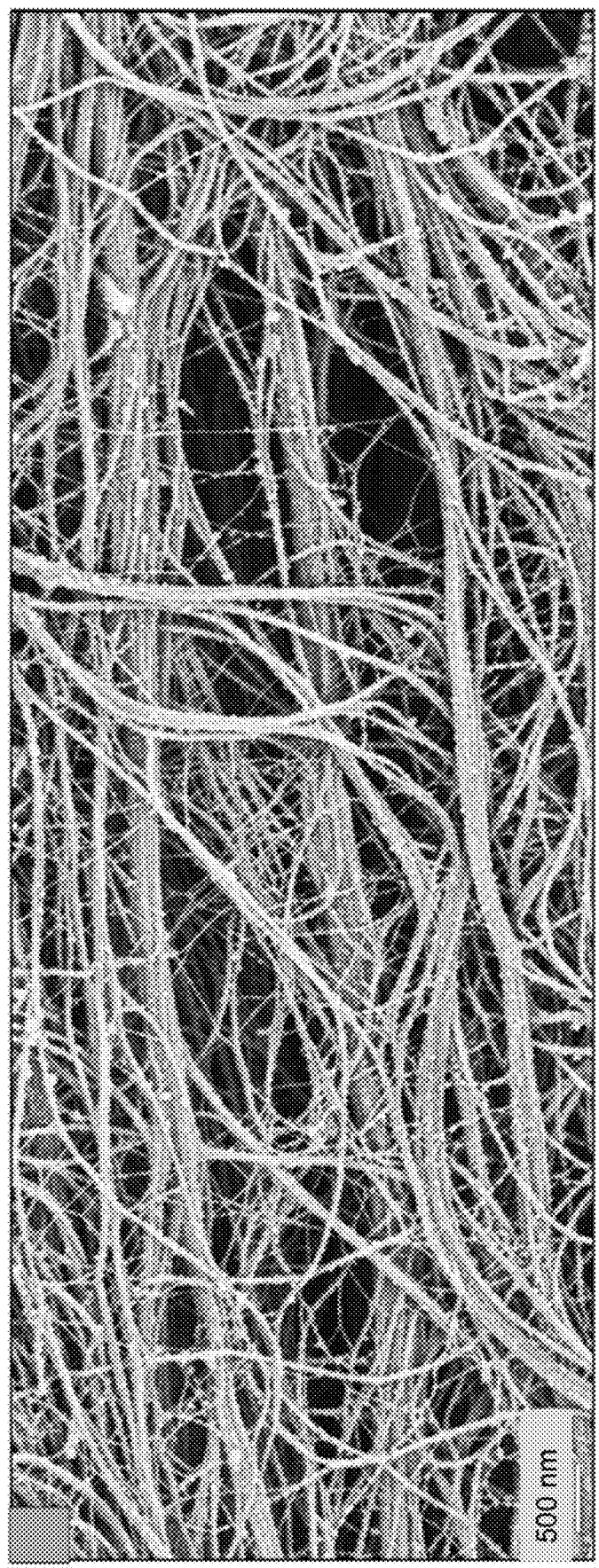
FIG. 25(C). SEM micrograph of a network of ECM, primarily collagen, from explanted HAPLGA 90° scaffold-tissue samples removed after 35 days in vivo.
Figure 25D:
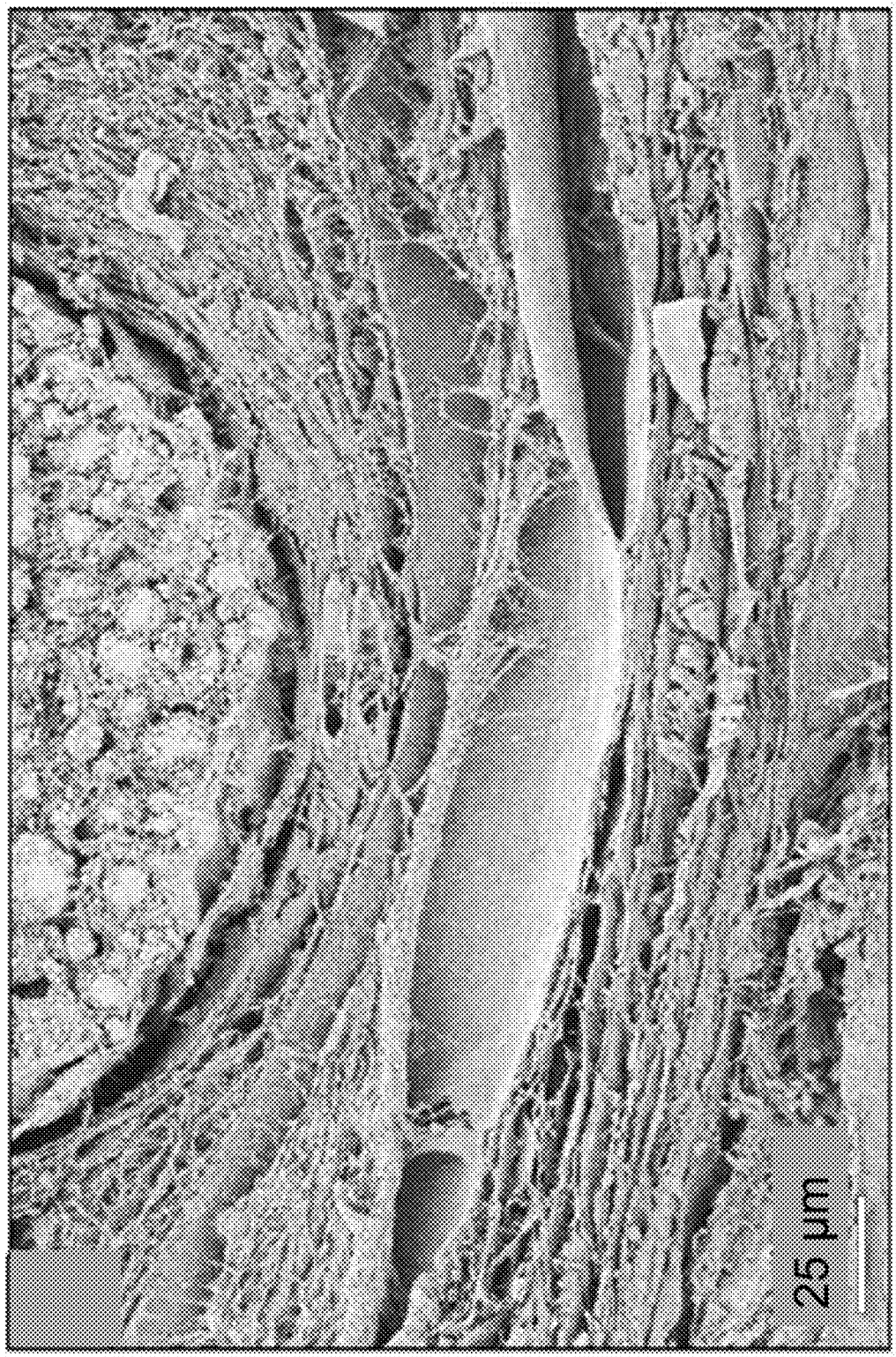
FIG. 25(D). SEM micrograph of an artery-vein complexes (dotted box) in close proximity to the HAPLGA material from explanted HAPLGA 90° scaffold-tissue samples removed after 35 days in vivo.
Figure 25E:
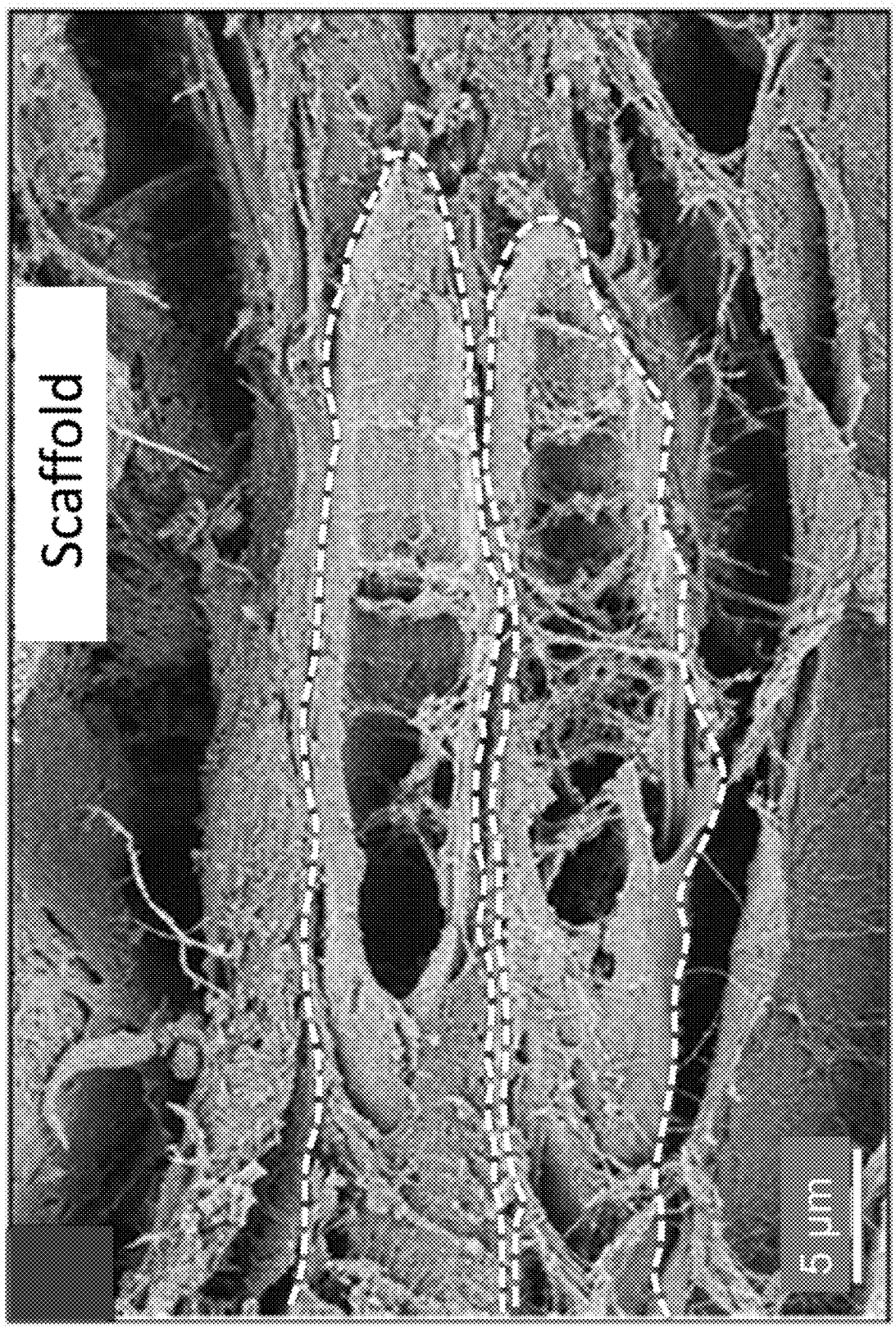
FIG. 25(E). SEM micrograph showing upper dotted line=blood vessel, lower dotted line=vein from explanted HAPLGA 90° scaffold-tissue samples removed after 35 days in vivo.

FIG. 24A-24C show SEM micrographs of explanted HAPLGA tissue growth scaffolds at different magnifications for samples removed after 35 days in vivo. The in-grown tissue forms intimate contact with the 3D-printed struts throughout the scaffold volume. The material of FIG. 24A is open and contains many more small and large vessels. The dotted circles in the magnified image shown in FIG. 24B are healthy red blood cells. A larger image of healthy red blood cells is provided in FIG. 24C.

FIG. 25 shows the SEM micrographs of explanted HAPLGA 90° scaffold-tissue samples removed after 35 days in vivo. FIG. 25A is a cross-sectional view of a single HAPLGA strut within the scaffold surrounded by in-grown tissue and active vessels (arrow and circles). The vasculature was active up until the point the scaffold-tissue sample was fixed and cut in half, as can be seen by the cut blood vessel which was in the middle of transporting red blood cells as well as other cells (FIG. 25B,monocyte, arrows). A network of ECM, primarily collagen, was observed to comprise the majority of tissue within the scaffold volume (FIG. 25C). Artery-vein complexes (FIG. 25D, dotted box) were also observed in close proximity to the HAPLGA material (FIG. 25E, upper dotted line=blood vessel, lower dotted line=vein).

Figure 26B:
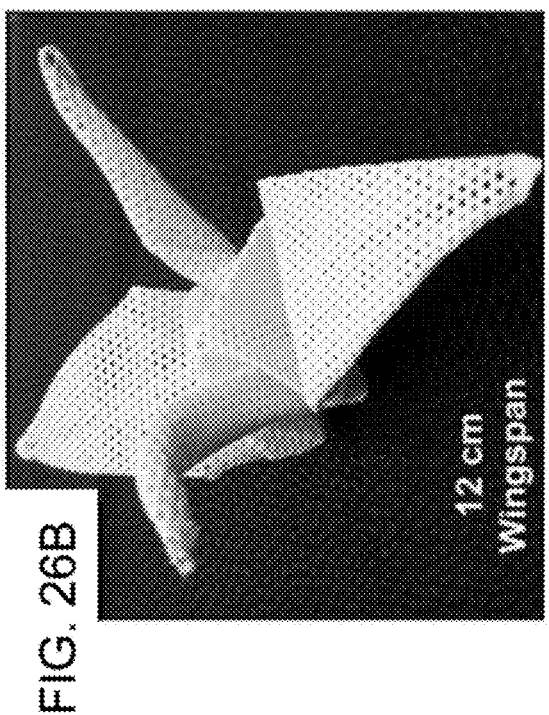
FIG. 26(B). HAPLGA sheets folded into a crane.
Figure 26A:
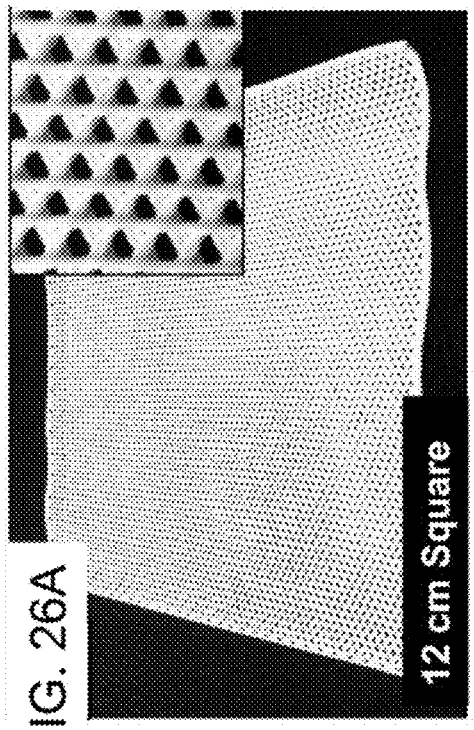
FIG. 26(A). HAPLGA 12×12 cm mesh sheet comprised of three layers (inset shows close up detail of 3DP pattern).
Figure 26C:
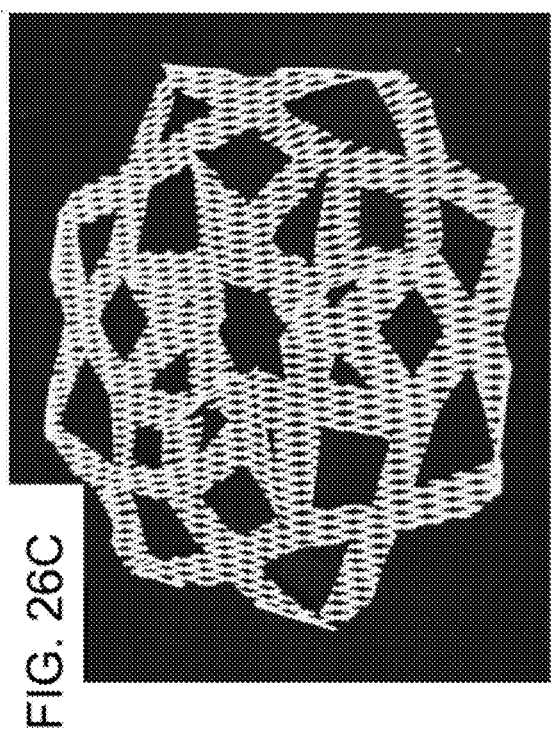
FIG. 26(C). HAPLGA snowflake created through folding a two-layer 20° HAPLGA sheet and selectively cutting along folds to create a radially symmetric pattern.

Mechanical Flexibility:

The mechanical flexibility of sheets printed from the HAPLGA-based ink compositions was demonstrated by rolling, folding and cutting the sheets. FIG. 26A shows a 12×12 cm mesh sheet comprised of three layers printed from an HAPLGA ink (inset shows close up detail of 3DP pattern). FIG. 26B shows that the printed HAPLGA sheets can be folded to create a complex structure such as a crane. FIG. 26C is a snowflake created through folding a two-layer 20° HAPLGA sheet and selectively cutting along folds to create a radially symmetric pattern.

Figure 27:
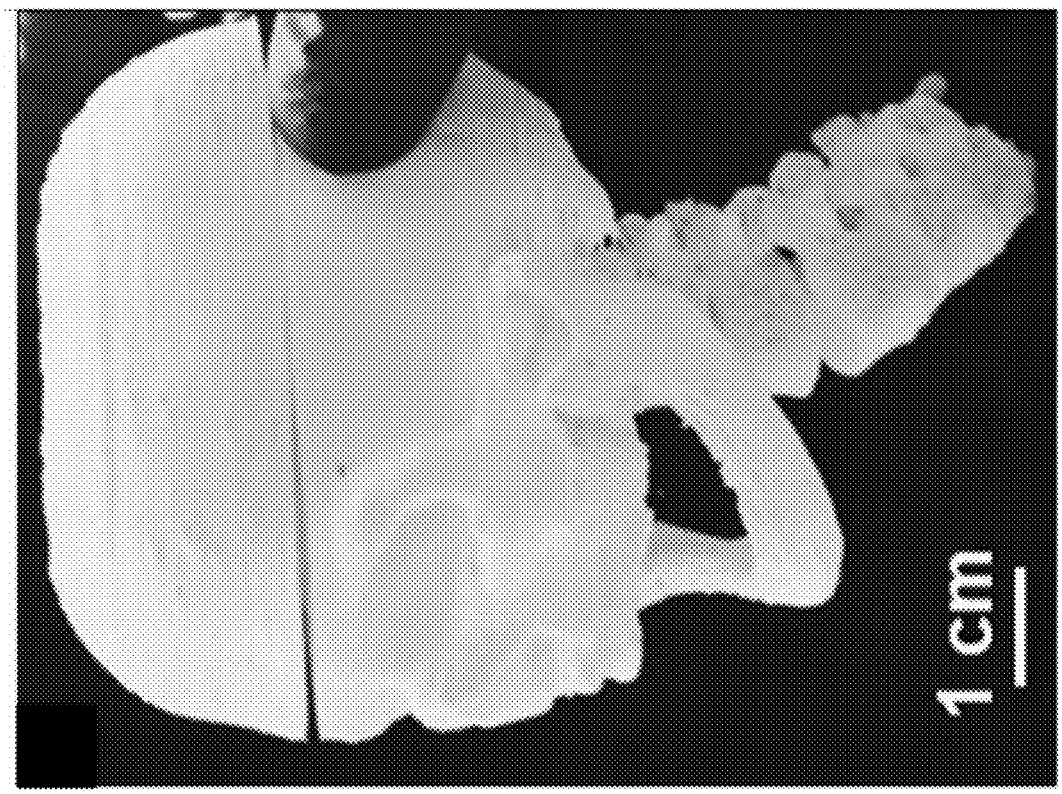
FIG. 27. A skull with spine produced by printing the skull and spine separately, followed by fusing the spine to the base skull via application of an HAPLGA ink to edges of the contacting regions.

Use of Inks as Adhesives:

To illustrate the ability of the ink compositions to act as adhesives in bonding pre-fabricated parts into a single object, a skull with a spine was produced by printing the skull and spine separately using an HAPLGA ink, followed by fusing the spine to the base skull via application of an HAPLGA ink to edges of the contacting regions. The skull in this case was approximately 340 printed layers thick (not including the spine). The spine itself was printed in two separate sections (halves along its length). The spine halves were fused together using the HAPLGA ink, dispensed via syringe by hand, along the seams. The spine was then fused to the skull using the HAPLGA ink, by dispensing the ink via syringe by hand to the base of the skull and contacting the spine to the ink. Finally, the jaw was printed separately and fused to the skull using the HAPLGA ink as an adhesive. The resulting skull and spine are shown in FIG. 27. The fabrication of the skull and spine illustrates the scalability of the printing to produce a large complex object comprising hundreds of printed layers and also illustrates the ability of the ink compositions to seamlessly fuse independently printed parts.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A solvent-based 3D printed porous tissue growth material comprising at least one layer formed from a solvent-based ink extruded at room temperature with the solvent evaporated upon extruding, the at least one layer comprises one or more porous fibers, a microstructure of the one or more porous fibers is a continuous matrix of a biocompatible polymer binder with intra fiber pores and bioactive ceramic particles dispersed throughout the microstructure, the bioactive ceramic particles make up at least 70 weight percent of the one or more porous fibers, and the one or more porous fibers are osteogenically active and can undergo a reversible deformation when a compressive or tensile stress is applied and then removed.

2. The material of claim 1 comprising a plurality of stacked layers, each layer in the plurality of stacked layers comprising one or more of the porous fibers.

3. The materials of claim 1 comprising a plurality of the porous fibers.

4. The material of claim 1, wherein the bioactive ceramic particles make up at least 90 weight percent of the porous fibers.

5. The material of claim 1, wherein the bioactive ceramic particles are calcium phosphate particles.

6. The material of claim 5, wherein the biocompatible polymer binder comprises polylactic-co-glycolic acid or polylactide-co-glycolide.

7. The material of claim 5, wherein the biocompatible polymer binder comprises polycaprolactone.

8. The material of claim 3, wherein the porous fibers in the material are spaced apart and run parallel with one another.

9. The material of claim 1, wherein the at least some portions of the one or more porous fibers run parallel with one another and are in contact along their long axes.

10. The material of claim 1, wherein the one or more porous fibers include intra fiber pores with diameters in the range from about 1 μm to about 10 μm.

11. The material of claim 1, wherein the one or more porous fibers each have a diameter greater than 100 μm.

12. The material of claim 11, wherein the one or more porous fibers each have a diameter of less than 400 μm.

13. The material of claim 3, wherein the porous fibers are spaced apart and intra-scaffold pores are defined by spaces between the fibers, the intra-scaffold pores having diameters of greater than 200 μm.

14. The material of claim 1 further comprising living cells seeded into the material.

15. The material of claim 14, wherein the living cells comprise mesenchymal stem cells.

16. The material of claim 1, characterized in that it can undergo a deformation from an original shape to a deformed shaped under a compressive stress.

17. The material of claim 1, wherein the biocompatible polymer binder comprises an elastomeric polymer.

18. The material of claim 17, wherein the biocompatible polymer binder comprises polylactic-co-glycolic acid, polylactide-co-glycolide, or polycaprolactone.

19. The material of claim 18, wherein the bioactive ceramic particles make up at least 80 weight percent of the porous fibers.

20. The material of claim 1, wherein the shape of the tissue growth material can undergo a 55% compression when a compressive stress is applied and rebound to its original shape when the compressive stress is removed.

21. The material of claim 1, wherein the shape of the tissue growth material can undergo a 40% stretch when a tensile stress is applied and rebound to its original shape when the tensile stress is removed.

22. The material of claim 1, wherein the biocompatible polymer binder comprises a biodegradable polymer.

23. The material of claim 1, wherein the material consists essentially of the one or more porous fibers, the bioactive ceramic particles, optionally, at least one bioactive factor without heat induced degradation, and, optionally, plasticizers.

24. The material of claim 1, wherein at least one bioactive factor is incorporated directly into the continuous matrix of the porous tissue growth material without heat induced degradation.

25. The material of claim 24, wherein the at least one bioactive factor is a protein, peptide, growth factor and gene, pharmaceutical compound, or combination thereof.

26. The material of claim 1, wherein the one or more porous fibers that are incompressible solid structures have a wet density of at least 1.97 g/cm$^3$ or a dry density of 1.47 g/cm$^3$.

27. A method of growing cells, tissue, or both using the material of claim 1, the method comprising seeding the material with living cells, and culturing the cell-seeded material in a cell or tissue growth culture medium.

28. A method of promoting in vivo tissue growth on the material of claim 1, the method comprising implanting the material into a living animal.

29. The method of claim 28, wherein the animal is a human.

30. The method of claim 28, wherein the material comprises a plurality of stacked layers, each layer in the plurality of stacked layers comprising one or more of the porous fibers.

31. A solvent-based 3D printed porous tissue growth material comprising at least one layer comprising one or more porous fibers, the one or more porous fibers are a continuous matrix of a biocompatible polymer binder with a microstructure formed from a solvent-based ink extruded at room temperature with the solvent evaporated upon extruding and with intra fiber pores and bioactive ceramic particles dispersed throughout the microstructure, the bioactive ceramic particles make up at least 70 weight percent of the one or more porous fibers, the biocompatible polymer binder makes up from 10 weight percent to 30 weight percent of the combined weight of the bioactive ceramic particles and the biocompatible polymer binder, and one or more porous fibers are osteogenically active and can undergo a reversible deformation when a compressive or tensile stress is applied and then removed.

32. A solvent-based 3D printed porous tissue growth material comprising at least one layer comprising one or more porous fibers, the one or more porous fibers are formed from a solvent-based ink extruded at room temperature with the solvent evaporated upon extruding to form a microstructure with a continuous matrix of a biocompatible polymer binder with intra fiber pores and bioactive ceramic particles dispersed throughout the microstructure, the bioactive ceramic particles make up at least 70 weight percent of the one or more porous fibers, one or more porous fibers are osteogenically active and can undergo a reversible deformation when a compressive or tensile stress is applied and then removed, and the bioactive ceramic particles are dispersed in the continuous matrix of the biocompatible binder that allows the bioactive ceramic particles to translate upon mechanical loading and return to their original position upon unloading.

33. A solvent-based 3D printed porous tissue growth material comprising at least one layer comprising one or more porous fibers with a microstructure formed from a solvent-based ink extruded at room temperature with the solvent evaporated upon extruding, the one or more porous fibers have a diameter greater than 100 μm and a continuous matrix of a biocompatible polymer binder with intra fiber pores and bioactive ceramic particles dispersed throughout the microstructure, the bioactive ceramic particles make up at least 70 weight percent of the one or more porous fibers, and the one or more porous fibers are osteogenically active and can undergo a reversible deformation when a compressive or tensile stress is applied and then removed.

* * * * *